United States Patent
Fauver et al.

(10) Patent No.: US 7,907,765 B2
(45) Date of Patent: Mar. 15, 2011

(54) FOCAL PLANE TRACKING FOR OPTICAL MICROTOMOGRAPHY

(75) Inventors: Mark E. Fauver, Seattle, WA (US); Eric J. Seibel, Seattle, WA (US); Michael G. Meyer, Seattle, WA (US); Alan C. Nelson, Gig Harbor, WA (US); J. Richard Rahn, Sammamish, WA (US); Thomas Neumann, Seattle, WA (US); Roger H. Johnson, Phoenix, AZ (US)

(73) Assignees: University of Washington, Seattle, WA (US); Visiongate, Inc., Pheonix, AZ (US)

( * ) Notice: Subject to any disclaimer, the term of this patent is extended or adjusted under 35 U.S.C. 154(b) by 1213 days.

(21) Appl. No.: 11/532,648

(22) Filed: Sep. 18, 2006

(65) Prior Publication Data
US 2010/0322494 A1 Dec. 23, 2010

Related U.S. Application Data

(63) Continuation-in-part of application No. 11/203,878, filed on Aug. 15, 2005, now abandoned, which is a continuation-in-part of application No. 10/308,309, filed on Dec. 3, 2002, now Pat. No. 6,944,322, which is a continuation-in-part of application No. 09/927,151, filed on Aug. 10, 2001, now Pat. No. 6,522,775.

(60) Provisional application No. 60/279,244, filed on Mar. 28, 2001.

(51) Int. Cl.
*G06K 9/00* (2006.01)

(52) U.S. Cl. ......................... 382/131; 382/132

(58) Field of Classification Search ........... 382/128–132
See application file for complete search history.

(56) References Cited

U.S. PATENT DOCUMENTS

| | | | |
|---|---|---|---|
| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeless, Jr. |
| 3,748,468 A | 7/1973 | Hartman |
| 3,833,762 A | 9/1974 | Gudmundsen |

(Continued)

FOREIGN PATENT DOCUMENTS
JP 02085747 A 3/1990

(Continued)

OTHER PUBLICATIONS

Fauver et al., "Three-dimensional imaging of single isolated cell nuclei using optical projection tomography," Optics Express, May 30, 2005/vol. 13, No. 11/4210-4223.

(Continued)

*Primary Examiner* — Wesley Tucker
(74) *Attorney, Agent, or Firm* — Citadel Patent Law; George A. Leone

(57) ABSTRACT

An optical tomography system for imaging an object of interest including a light source for illuminating the object of interest with a plurality of radiation beams. The object of interest is held within an object containing tube such that it is illuminated by the plurality of radiation beams to produce emerging radiation from the object containing tube, a detector array is located to receive the emerging radiation and produce imaging data used by a mechanism for tracking the object of interest.

3 Claims, 21 Drawing Sheets

U.S. PATENT DOCUMENTS

| | | |
|---|---|---|
| 3,960,449 A | 6/1976 | Carlton |
| 3,999,047 A | 12/1976 | Green |
| 4,175,860 A | 11/1979 | Bacus |
| 4,183,623 A | 1/1980 | Haines |
| 4,200,353 A | 4/1980 | Hoffman |
| 4,293,221 A | 10/1981 | Kay |
| 4,360,885 A | 11/1982 | Edgar |
| 4,714,345 A | 12/1987 | Schrader |
| 4,858,128 A | 8/1989 | Nowak |
| 4,873,653 A | 10/1989 | Grosskopf |
| 4,891,829 A | 1/1990 | Deckman |
| 5,141,609 A | 8/1992 | Sweedler |
| 5,148,502 A | 9/1992 | Tsujiuchi |
| 5,281,517 A | 1/1994 | Bacus |
| 5,308,990 A | 5/1994 | Takahashi |
| 5,312,535 A | 5/1994 | Waska |
| 5,321,501 A | 6/1994 | Swanson |
| 5,333,164 A | 7/1994 | Tam |
| 5,402,460 A | 3/1995 | Johnson |
| 5,428,447 A * | 6/1995 | Toida ............................ 356/601 |
| 5,539,800 A | 7/1996 | Katsevich |
| 5,548,395 A | 8/1996 | Kosaka |
| 5,552,605 A | 9/1996 | Arata |
| 5,668,887 A | 9/1997 | Parker |
| 5,673,300 A | 9/1997 | Reckwerdt |
| 5,680,484 A | 10/1997 | Ohyama |
| 5,710,429 A | 1/1998 | Alfano |
| 5,741,411 A | 4/1998 | Yeung |
| 5,760,901 A | 6/1998 | Hill |
| 5,760,951 A | 6/1998 | Dixon |
| 5,828,408 A | 10/1998 | Mottin |
| 5,848,123 A | 12/1998 | Strommer |
| 5,878,103 A | 3/1999 | Sauer |
| 5,880,838 A | 3/1999 | Marx |
| 5,909,476 A | 6/1999 | Cheng |
| 5,915,048 A | 6/1999 | Hill |
| 5,987,158 A | 11/1999 | Meyer |
| 6,005,617 A | 12/1999 | Shimamoto |
| 6,026,174 A | 2/2000 | Palcic |
| 6,037,579 A | 3/2000 | Chan et al. |
| 6,038,067 A | 3/2000 | George |
| 6,047,080 A | 4/2000 | Chen |
| 6,072,624 A | 6/2000 | Dixon |
| 6,078,681 A | 6/2000 | Silver |
| 6,091,983 A | 7/2000 | Alfano |
| 6,130,958 A | 10/2000 | Rohler |
| 6,165,734 A | 12/2000 | Garini |
| 6,192,144 B1 | 2/2001 | Holz |
| 6,201,628 B1 | 3/2001 | Basiji |
| 6,211,955 B1 | 4/2001 | Basiji |
| 6,215,587 B1 | 4/2001 | Alfano |
| 6,239,871 B1 | 5/2001 | Gilby |
| 6,248,988 B1 | 6/2001 | Krantz |
| 6,249,341 B1 | 6/2001 | Basiji |
| 6,251,586 B1 | 6/2001 | Mulshine |
| 6,251,615 B1 | 6/2001 | Oberhardt |
| 6,252,979 B1 | 6/2001 | Lee |
| 6,312,914 B1 | 11/2001 | Kardos |
| 6,388,809 B1 | 5/2002 | MacAulay |
| 6,452,179 B1 | 9/2002 | Coates |
| 6,519,355 B2 | 2/2003 | Nelson |
| 6,522,775 B2 | 2/2003 | Nelson |
| 6,529,614 B1 | 3/2003 | Chao |
| 6,591,003 B2 | 7/2003 | Chu |
| 6,636,623 B2 | 10/2003 | Nelson |
| 6,640,014 B1 | 10/2003 | Price |
| 6,697,508 B2 | 2/2004 | Nelson |
| 6,741,730 B2 | 5/2004 | Rahn |
| 6,770,893 B2 | 8/2004 | Nelson |
| 6,775,399 B1 | 8/2004 | Jiang |
| 6,850,587 B1 | 2/2005 | Karimi |
| 6,868,177 B1 | 3/2005 | Camahort |
| 6,944,322 B2 | 9/2005 | Johnson |
| 6,991,738 B1 | 1/2006 | Fauver |
| 7,003,143 B1 | 2/2006 | Hewitt |
| 2001/0012069 A1 | 8/2001 | Derndinger |
| 2002/0161534 A1 | 10/2002 | Adler |
| 2003/0199758 A1 | 10/2003 | Nelson |
| 2003/0222197 A1 | 12/2003 | Reese |
| 2004/0001618 A1 | 1/2004 | Johnson et al. |
| 2004/0008515 A1 | 1/2004 | Brown |
| 2004/0076319 A1 | 4/2004 | Fauver |
| 2005/0006595 A1 | 1/2005 | Goodwin |
| 2005/0010108 A1 | 1/2005 | Rahn |
| 2005/0085708 A1 | 4/2005 | Fauver |
| 2005/0085721 A1 | 4/2005 | Fauver |
| 2006/0023219 A1 | 2/2006 | Meyer |
| 2006/0096358 A1 | 5/2006 | Fauver et al. |
| 2006/0099707 A1 | 5/2006 | Nelson |
| 2006/0183220 A1 | 8/2006 | Nelson |

FOREIGN PATENT DOCUMENTS

| | | |
|---|---|---|
| JP | 10260131 A | 9/1998 |
| JP | 2000121550 A | 4/2000 |
| WO | WO0111341 A2 | 2/2002 |
| WO | WO0218537 A2 | 3/2002 |
| WO | WO0235474 A1 | 5/2002 |
| WO | WO02095476 A2 | 11/2002 |

OTHER PUBLICATIONS

Fauver et al., "Development of Micro-Optical Projection Tomography for 3D Analysis of Single Cells, " Image Acquisition and Processing XI. Edited by Conchello, Jose-Angel; Cogswell, Carol J.; Wilson, Tony. Proceedings of the SPIE, vol. 5324, pp. 171-181 (2004).

Zaidi, H. and Hasegawa, B., Determination of the Attenuation Map in Emission Tomography, The Journal of Nuclear Medicine, Special Contributions, vol. 44, No. 2, Feb., 291-315, 2003.

Kikuchi, S. et al., "Three-dimensional computed tomography for optical microscopes," Optics Communications 107 (1994) 432-444.

Kikuchi, S. et al., "Three-dimensional microscopic computed tomography based on general Radon transform for optical imaging systems," Optics Communications 123 (1996) 725-733.

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-382, 1987.

Gilbert, P, "Iterative Methods for the Three dimensional Reconstruction of an Object from Projections," Journal of Theoretical Biology 36pp. 105-117, 1972.

Oppenheim, BE, "More Accurate Algorithms for Iterative 3 dimensional Reconstruction," IEEE Transactions on Nuclear Science NS-21pp. 72-7, 1974.

Singer, Jr, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "ART is Science being a Defense of Algebraic Reconstruction Techniques for Three dimensional Electron Microscopy," Journal of Theoretical Biology 32pp. 205-216, 1971.

Manglos,SH, Jaszcak, RJ, and Floyd, CE, "Maximum Likelihood Reconstruction for Cone Beam SPECT: Development and Initial Tests," Physics in Medicine and Biology 34(12)pp. 1947-1957, 1989, #1382.

Manglos,SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-193,1998.

Herman, G, Image Reconstruction from Projections: The Fundamentals of Computerized Tomography, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, Practical Flow Cytometry, 3rd ed., Wiley-Liss, 1995.

HJ Tiziani, and MI Uhde, Three-dimensional analysis by a microlens array confocal arrangements (Applied Optics 33, 567 [1994]).

Bayat, S, Le Duc, G, Porra, L, Berrruyer, G, Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282 (R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney,JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney,JH, and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," Science, vol. 296, pp. 541-545, Apr. 19, 2002.

Sharpe, J, review, "Optical Projection Tomography as a New Tool for Studying Embryo Anatomy," J. Anat. (2003), pp. 175-181.

RH Anderson, "Close-up imaging of documents and displays with lens arrays," AppliedOptics 18, 477 (1979).

Kak, A.C. and Slaney, M., Principles of Computerized Tomographic Imaging, IEEE Press, New York, 1988.

E.G. Steward, Fourier Optics: An Introduction, 2nd ed. (Halsted Press, New York, 1987).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al. "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements," Cytometry, vol. 2, No. 5, pp. 327-336 (1982).

M. Rozycka, et al., "Optical Diffraction as a Tool for Semiautomatic, Quantitative Analysis of Tissue Specimens," Cytometry, vol. 2, No. 4, pp. 244-248 (1982).

W.H. Press et al., Numerical Recipes in C (New York: Cambridge University Press, 1988).

Almeida and Fuji, Fourier transform differences and averaged simularities in diatoms, Applied Optics, vol. 18, No. 10, pp. 1663-1667, (1979).

Smolinska and Dawidowicz, "Extraction of common or different part from optical images," Institute of Physics, Warsaw Technical University, 222-223.

Pawley, JB, Handbook of Biological Confocal Microscopy, Plenum Press, NY, 479-490 (1995).

\* cited by examiner

FOCAL PLANE TRACKING FOR OPTICAL MICROTOMOGRAPHY

RELATED APPLICATION

This application claims priority from and is a continuation-in-part of co-pending U.S. application Ser. No. 11/203,878 of Meyer et al., filed Aug. 15, 2005, entitled "OPTICAL TOMOGRAPHY OF SMALL OBJECTS USING PARALLEL RAY ILLUMINATION AND POST-SPECIMEN OPTICAL MAGNIFICATION." that is in turn a continuation-in-part of U.S. Pat. No. 6,944,322 of Johnson and Nelson, issued Sep. 13, 2005, entitled "OPTICAL TOMOGRAPHY OF SMALL OBJECTS USING PARALLEL RAY ILLUMINATION AND POST-SPECIMEN OPTICAL MAGNIFICATION," that is in turn a continuation-in-part of U.S. Pat. No. 6,522,775 of Alan C. Nelson, issued Feb. 18, 2003, that is in turn related to the provisional application of Alan C. Nelson, Ser. No. 60/279,244, filed Mar. 28, 2001; both entitled "APPARATUS AND METHOD FOR IMAGING SMALL OBJECTS IN A FLOW STREAM USING OPTICAL TOMOGRAPHY." U.S. application Ser. No. 11/203,878 of Meyer et al, is hereby incorporated by reference. U.S. Pat. No. 6,944,322, and U.S. Pat. No. 6,522,775 are also hereby incorporated by reference.

STATEMENT REGARDING FEDERALLY SPONSORED RESEARCH

This invention was made with government support under SBIR Phase I Grant No. HHSN2612004330106 awarded by the National Institute of Health/National Cancer Institute (NIH/NCI). The government has certain rights in the invention.

FIELD OF THE INVENTION

The present invention relates to optical tomographic (OT) imaging systems in general, and, more particularly, to microscopic optical tomography where a small object, such as a biological cell, for example, is illuminated by a light beam in the visible or ultraviolet portion of the electromagnetic spectrum, rotated and tracked, and projected images are produced.

BACKGROUND OF THE INVENTION

A patent application of Fauver et al. published as US-2004-0076319-A1 on Apr. 22, 2004, incorporated herein by this reference, discloses a method and apparatus for continuously scanning the focal plane of an optical imaging system along an axis perpendicular to said plane through the thickness of a specimen during a single detector exposure.

One such method is accomplished by moving an objective lens, thereby scanning the focal plane through the thickness of the specimen region, such that the entire specimen thickness is scanned continuously during a single detector exposure interval. A pseudoprojection image is thereby generated whose resolution can depend on the depth of focus of a moving focal plane, as well as on the lateral spatial resolution (i.e., the resolution within the focal plane). The procedure is repeated from several perspectives over an arc of up to 180 degrees, using one or more pairs of light sources and detector arrays simultaneously. The specimen can be rotated and/or translated to acquire additional viewpoints. In this way, a set of pseudoprojections is generated, which can be input to a tomographic image reconstruction algorithm, such as filtered backprojection, to generate a three-dimensional image.

Known techniques work well for a specimen that is positioned in the center of a rotating capillary tube because the specimen will not move out of an initial focal plane during rotation. However, many specimens are positioned off center and will translate out of an initial focal plane. Such offset positions can cause focusing errors and adversely affect post-imaging acquisition reconstruction of the specimen.

SUMMARY OF THE INVENTION

The present invention provides an optical tomography system for imaging an object of interest including a light source for illuminating the object of interest with a plurality of radiation beams. The object of interest is held within an object containing tube such that it is illuminated by the plurality of radiation beams to produce emerging radiation from the object containing tube, a detector array is located to receive the emerging radiation and produce imaging data used by a mechanism for tracking the object of interest.

In one contemplated embodiment, a parallel ray beam radiation source illuminates the object of interest with a plurality of parallel radiation beams. An outer tube has an optically flat input surface for receiving the illumination and a concave output surface, where the concave outer surface acts as a magnifying optic to diverge the radiation emerging from the outer tube after passing through the object of interest. An object containing tube is located within the outer tube, wherein the object of interest is held within the object containing tube. A motor is coupled to rotate and otherwise manipulate the object containing tube to present differing views of the object of interest. A detector array is located to receive the emerging radiation from the concave output surface.

The present invention relates generally to three-dimensional optical tomography using parallel beam projections produced by a laser or other illumination system in conjunction with CCD or CMOS detectors and, more particularly, to three-dimensional tomographic imaging of microscopic objects, including biological cells, in a flow stream or entrained in a rigid medium.

BRIEF DESCRIPTION OF THE DRAWINGS

The accompanying drawings incorporated in and forming a part of the specification illustrate several aspects of the present invention, and together with the description, serve to explain the principles of the invention. Moreover, in the drawings, like reference numerals designate corresponding parts throughout the several views. In the drawings.

DETAILED DESCRIPTION OF THE PREFERRED EMBODIMENTS

Figure 1:
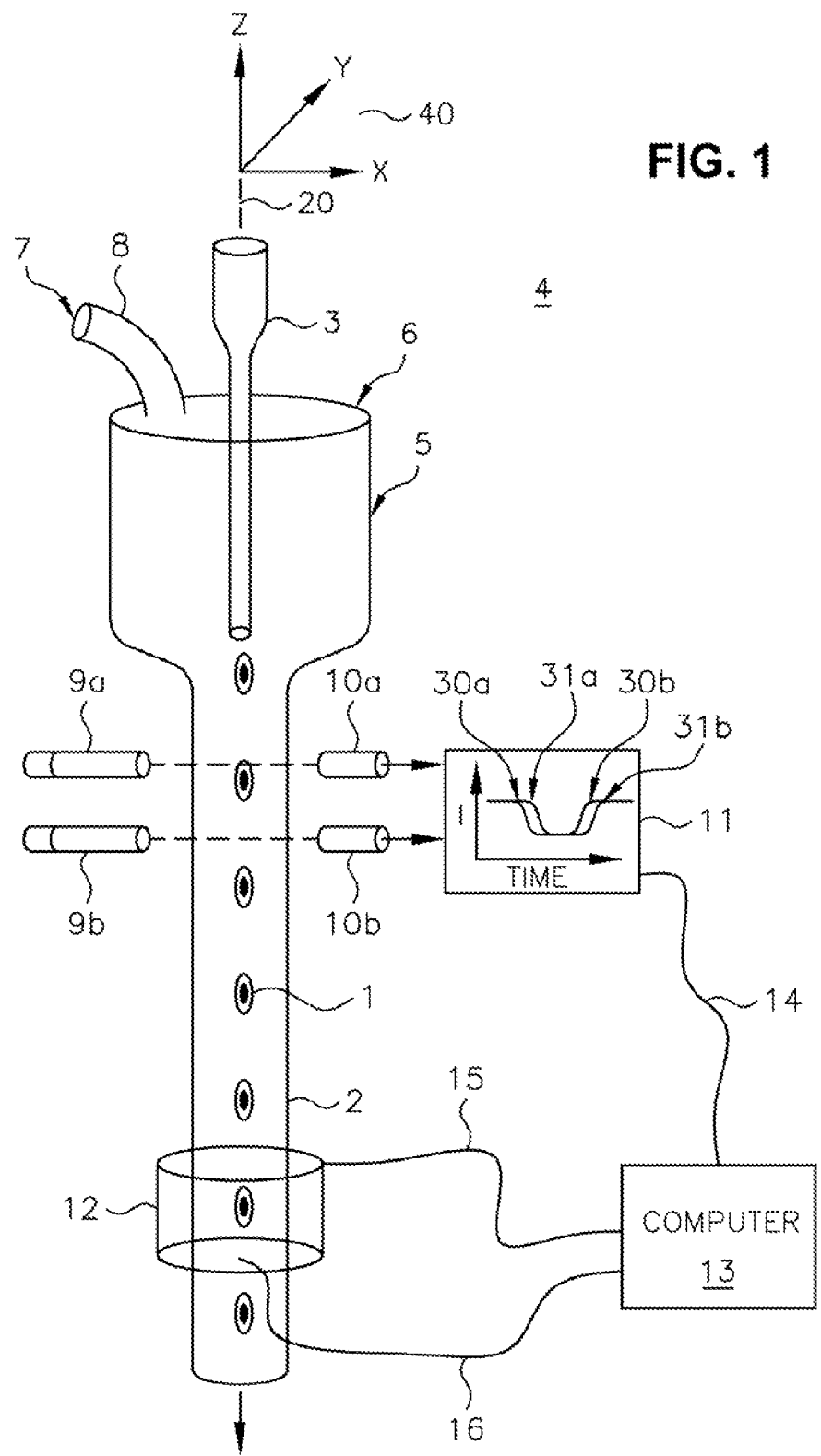
FIG. 1 schematically shows an example illustration of a Parallel Beam Flow Optical Tomography system as contemplated by an embodiment of the present invention.

Reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications, and equivalents included within the spirit and scope of the invention as defined by the appended claims.

The invention is further described herein with respect to specific examples relating to biological cells. It will be understood, however, that these examples are for the purpose of illustrating the principals of the invention, and that the invention is not so limited. In one example, constructing a three dimensional distribution of optical densities within a microscopic volume enables the quantification and the determination of the location of structures, molecules or molecular probes of interest. By using tagged molecular probes, the quantity of probes that attach to specific structures in the microscopic object may be measured. For illustrative purposes, an object such as a biological cell may be labeled with at least one stain or tagged molecular probe, and the measured amount and location of this probe may yield important information about the disease state of the cell, including, but not limited to, various cancers such as lung, breast, prostate, cervical and ovarian cancers.

Generally as used herein the following terms have the following meanings when used within the context of optical microscopy processes:

"Capillary tube" has its generally accepted meaning and is intended to include microcapillary tubes and equivalent items with an inside diameter of 100 microns or less. Such microcapillary tubes are manufactured by Polymicro Technologies, LLC., AZ.

"Object" means an individual cell or other entity. One or more objects may comprise a specimen.

"Pseudoprojection" includes a single image representing a sampled volume of extent larger than the native depth-of-field of the optics.

"Specimen" means a complete product obtained from a single test or procedure from an individual patient, (e.g., sputum submitted for analysis, a biopsy, or a nasal swab.) A specimen may be composed of one or more objects. The result of the specimen diagnosis becomes part of the case diagnosis.

"Sample" means a finished cellular preparation that is ready for analysis, including all or part of an aliquot or specimen.

In one example of the present invention, the chosen illumination is parallel, or nearly parallel, until after passage through the object volume that may contain the cell or other specimen or object to be imaged. After passage through the object, a post-specimen optic diverges the emergent pattern of light intensities in order to produce a magnified pattern of light intensities in any plane perpendicular to the system's optical axis and situated downstream from the post-specimen optic. However, the invention is not limited to parallel beam radiation and, in fact, the embodiments described herein are useful for many forms of illumination at venous wavelengths.

Referring to FIG. 1, there schematically shown is an example illustration of a Parallel Beam Flow Optical Tomography (PBOT) system as contemplated by an embodiment of the present invention. The invention provides an apparatus and method for imaging small objects in a flow stream or entrained in a rigid medium using optical point source or parallel beam projections, image sensors, such as, for example, time delay and integration (TDI) image sensors or CCD or CMOS solid state image sensors and the like, and tomographic image reconstruction. The optical tomography (OT) system includes in one example embodiment, a flow cytometer, including a reconstruction cylinder 12, positioned around object containing tube 2. The object containing tube 2 may, for example, comprise a cell entrainment tube wherein the cell is held in a gel, or a capillary tube for cell flow, depending on the type of optical tomography system.

The PBOT system 4 is oriented with reference to a coordinate system 40 having coordinates in the X, Y and Z-directions. In operation, an object of interest 1, such as, for example a cell, including a human cell, is injected into an injection tube 3. The object containing tube 2 may be wider at an injection end 5 and includes a pressure cap 6. A sheath fluid 7 is introduced at tube 8 to create laminar flow within the object containing tube 2. A first source of photons 9a and a first photo detector 10a work together with a pulse height analyzer 11 to operate as a triggering device. Pulse height analyzer 11 operates to provide a first signal 30a for the beginning or leading edge of an object, such as a cell, and a second signal 30b for the end or trailing edge of the object as it moves through the tube. The signals 30a, 30b, 31a and 31b are represented as a light intensity, "I" versus "TIME" function within pulse height analyzer 11. The pulse height analyzer 11 may be a conventionally designed electronic circuit or the like. The pulse height analyzer 11 generates a plurality of signals 14 that are sent to a computer 13 which, after a delay related to the velocity of the moving object and distance between the photo detector and the reconstruction cylinder 12, sends a trigger signal on line 15 to a reconstruction cylinder 12 to initiate and terminate data collection for that particular object of interest. Additionally, a second photon source 9b and a second photo detector 10b may advantageously be positioned at a known distance downstream from the first set such that an interval between the object triggering a third signal 31a and triggering a fourth signal 31b may advantageously be used to calculate the velocity of the object and also as a timing signal to synchronize the line transfer rate of a TDI image sensor. The timing signal is transmitted to computer 13 in the plurality of signals 14. The computer 13, which may be any useful personal computer or equivalent, in turn sends synchronization signals on line 16 to the reconstruction cylinder 12. It will be understood that lines 15 and 16 are representative of communication and control lines between the PBOT system and the computer that communicate data, image information, control signals and other signals between the computer and the PBOT system. In this way, for example, the movement of the object along the flow axis 20 may be matched by a rate of transfer of charge from one stage of a TDI sensor to the next, as described and shown in more detail below with reference to FIG. 7.

Figure 2:
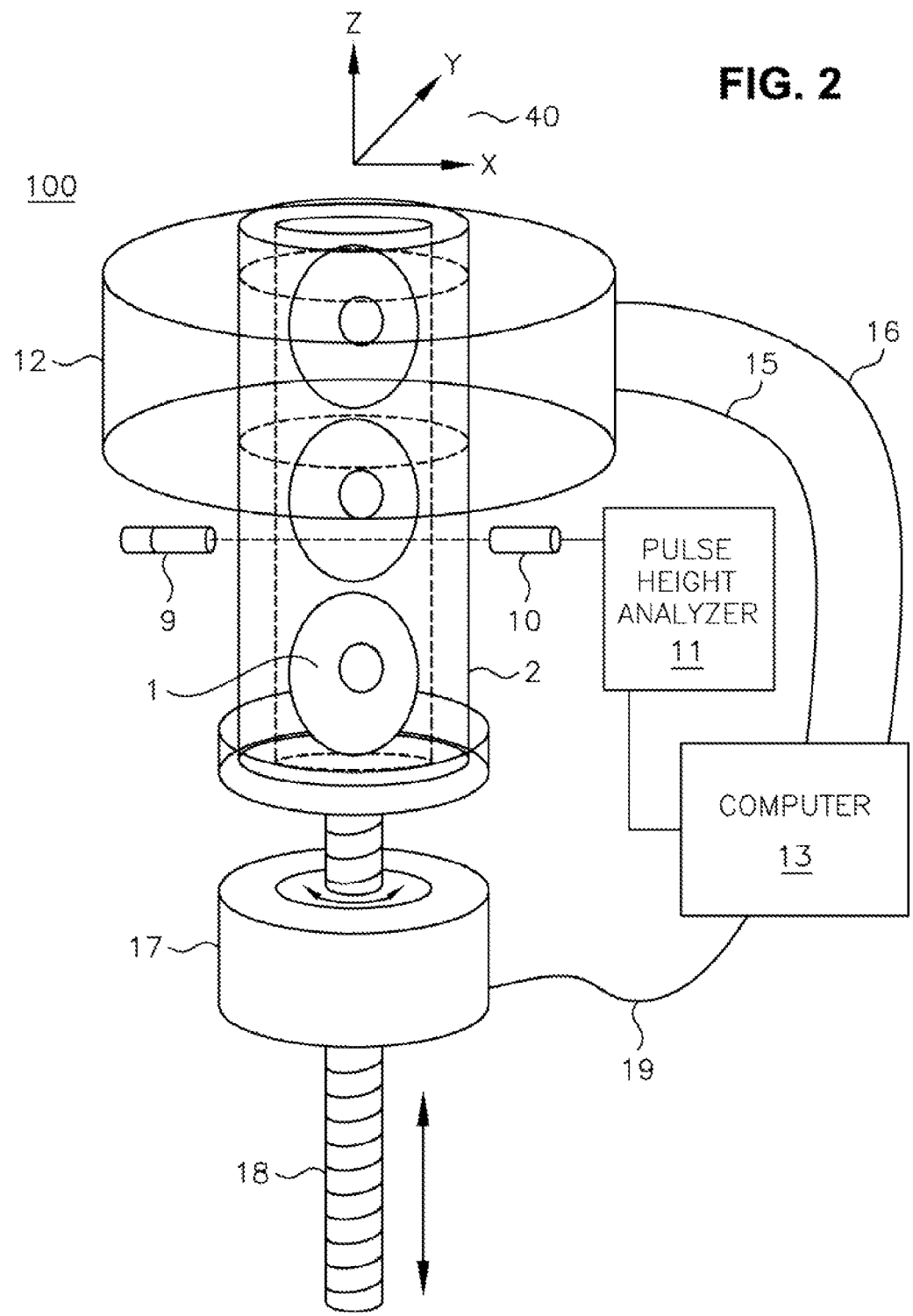
FIG. 2 schematically shows an example illustration of a Variable Motion Parallel Beam Optical Tomography system as contemplated by an embodiment of the present invention.

Now referring to FIG. 2, there schematically shown is an example illustration of a Variable Motion Parallel Beam Optical Tomography system as contemplated by one example embodiment of the present invention. A variable motion PBOT system 100 takes advantage of a mechanical positioner to present cells, which are entrained in a rigid medium in a tube, to the imaging system one at a time. As compared to the flow system described with reference to FIG. 1, in the variable motion PBOT system 100 only one trigger mechanism including a photon source 9 and a photo detector 10 is required since the velocity of the object, such as a human cell, can be precisely controlled to synchronize with the illumination sources and image sensors in the reconstruction cylinder 12. The trigger here is processed by the pulse height analyzer 11 and the computer 13 and used to start and stop data collection. The pulse height analyzer 11 is an electronic circuit of design similar to pulse height analyzer 11 except that it requires fewer inputs and outputs. As indicated by double arrow line the object containing tube 2 in this embodiment is translated along the z-axis through the reconstruction cylinder 12 by a screw drive 18 driven by a computer controlled motor 17. The object contained in tube 2 may also be rotated about the z-axis by the computer controlled motor 17. The computer controlled motor 17 receives control information 19 from the computer 13. It will be understood by those skilled in the art having the benefit of this disclosure, that any mechanism capable of translating and rotating the object containing tube 2 can be used in place of the screw drive. Signals from the reconstruction cylinder 12 may be analyzed directly or processed using image processing, image analysis and/or computerized tomographic image reconstruction techniques to provide two dimensional or three dimensional information about cells and other objects of interest.

Figure 3:
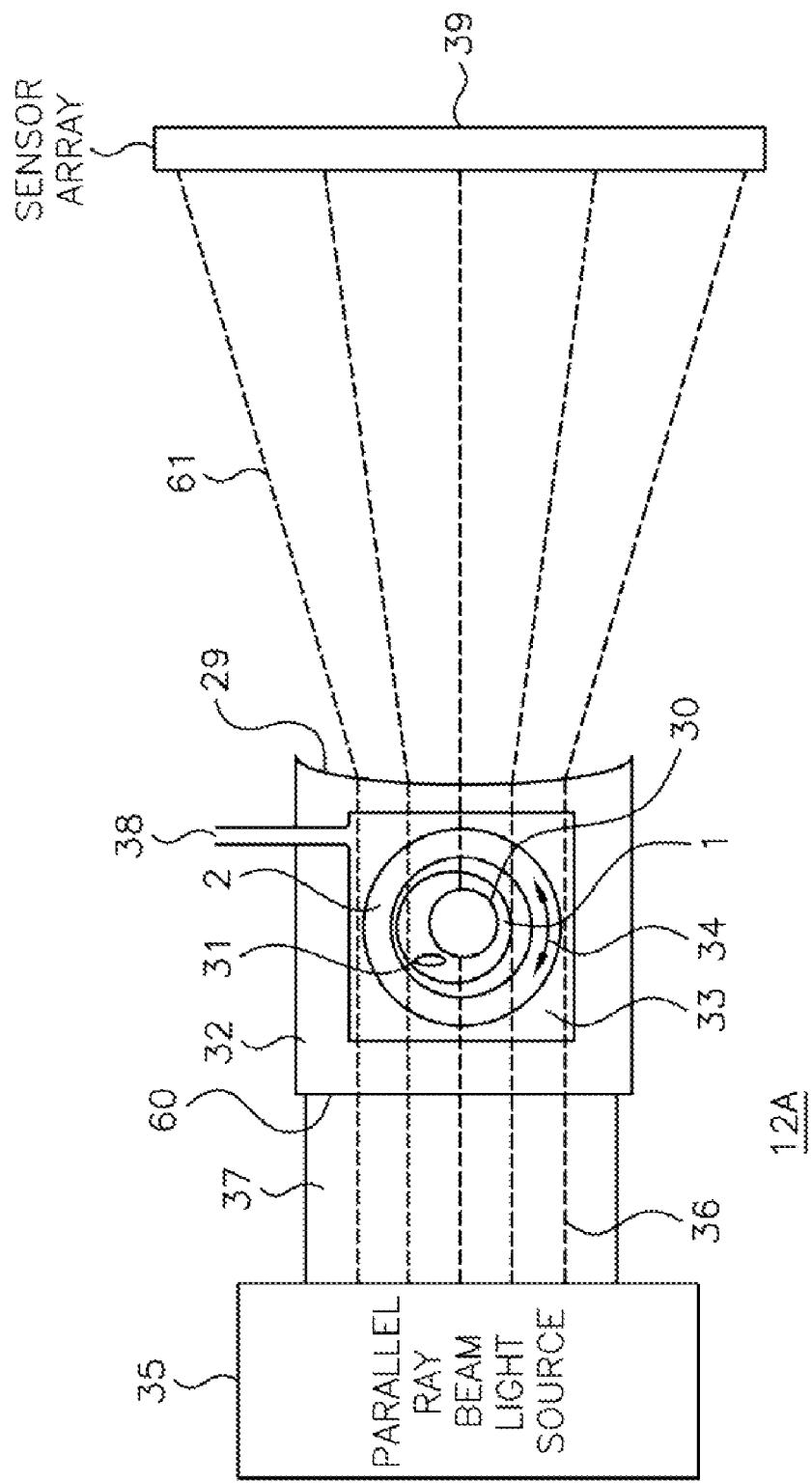
FIG. 3 schematically shows an example illustration of a system illumination geometry, including a single source-magnifying concave optic pair as contemplated by one example embodiment of the present invention.

Referring now to FIG. 3, a system illumination geometry within a reconstruction cylinder 12A for use in a parallel-beam optical tomography system for imaging an object of interest 1 is shown schematically. The reconstruction cylinder 12A includes a parallel ray beam radiation source 35 for illuminating the object of interest 1 with a plurality of parallel radiation beams 36. An outer tube 32 has an optically flat input surface 60 and a concave output surface 29, where the concave outer surface 29 diverges radiation 61 emerging from the outer tube 32 after passing through the object of interest 1. An object containing tube 2 is located within the outer tube 32, wherein the object of interest 1 is held within the object containing tube 2.

A motor, here indicated schematically as double arrow 34, is coupled to rotate the object containing tube 2 to present differing views of the object of interest 1. A detector array 39 is located to receive the emerging radiation 61 from the concave output surface 29. In one embodiment, the parallel ray beam radiation source 35 comprises a laser. In another example embodiment, the laser may be selected to emit radiation in the visible portion of the electromagnetic spectrum. In yet another example embodiment, the laser may be selected to emit radiation in the ultraviolet portion of the electromagnetic spectrum. The detector array 39 may advantageously comprise a sensor selected from the group consisting of solid state sensors, charge coupled device (CCD) sensors, complementary metal oxide semiconductor (CMOS) sensors and time delay and integration sensors.

In another embodiment of the present invention, a cell or other object to be imaged is present either in a flow tube, capillary tube, linear container, or in an entrainment tube. In one embodiment of the parallel-beam optical tomography system the object of interest 1 comprises a human cell having a nucleus 30. The cell may also contain subcellular features or constituents. At least one fluorescing or absorbing molecular probe 31 may be bound to one or more cellular constituents.

The object containing tube 2, for example a flow tube, capillary tube, linear container, or entrainment tube, is located substantially concentrically within the outer tube 32 which has a substantially rectangular outer cross section, and may have either a rectangular or circular inner cross section. Other cross sectional geometries for the outer tube 32 are possible. The curved surface of the object containing tube 2 acts as a cylindrical lens producing a focusing effect that may not be desirable in a projection system. Those skilled in the art having the benefit of this disclosure will appreciate that the bending of photons by the object containing tube 2 can be substantially reduced if the spaces 37 and 33 between the source and the outer tube 32 and between the tube 32 and the detector surfaces 39 are filled with a material having an index of refraction matching that of the object containing tube 2. Further, the tube can be optically coupled to the space filling material. Such optical coupling may be accomplished with oil or a gel, for example. An index of refraction-matching fluid in space 33, such as oil, for example, may advantageously be introduced through port 38 to entirely fill the space between the tube 2 in which the cells or other microscopic objects are contained and the outer tube 32. The index of refraction matching fluid, both tubes 2 and 32, and any gel or flowing liquid medium surrounding the cells to be imaged have identical, or nearly identical indices of refraction. The object contained within tube 2 may be rotated and/or translated within the index of refraction matching fluid and outer tube 32 with both axial and rotational motions under computer control.

In operation, a laser or other light source 35 produces parallel illuminating beams 36, which impinge on the outer tube 32, optionally delivered by an index of refraction-matched coupling element 37. In the absence of scatter, the light traverses parallel ray paths through both tubes 2 and 32. Since the refractive indices of all materials in the light path are matched, the rays traversing the index of refraction matching fluid and the object space within the volume to be imaged are parallel. Both tubes 2 and 32 comprise transparent, or nearly transparent material with respect to the illuminating wavelength. Both tubes 2 and 32 may comprise fused silica, glass or other similar optical material.

The exit face 29 of the outer, rectangular tube 32 may advantageously be provided with a diverging or magnifying optic, which, in one contemplated embodiment, may be a circularly symmetric polished depression, or dimple, in the fused silica or other optical material. The dimple acts as a plano-concave lens, causing the light ray paths 61 to become divergent at its exit surface 29. Such a dimple or any other optical element or combination of optical elements, including multiplets, or other equivalent elements, designed to perform the same function is referred to herein as a post-specimen optic. The post-specimen optic comprises, generally, a magnifying optic.

Using known optical design principles, the radius of curvature of the post-specimen optic may be determined and designed to impart the desired degree of divergence to the exiting light ray paths 61. The degree of divergence, together with the distance between the post-specimen optic and the TDI, CCD, CMOS or other image sensor 39, determines the magnification of the projection images. The magnification required is determined by the relationship between the desired spatial resolution of the projection images and the detector pixel size, and it is advantageous for the magnification to be much larger than twice the quotient of the pixel size and the desired spatial resolution of the projection.

For example, in one contemplated embodiment of the present invention, if the desired spatial resolution in the projections is 0.5 micron and the detector pixel size is 10 microns, it is advantageous for the magnification to be significantly larger than 40 times. In this example, it may be desirable for the magnification to be 80 times, 100 times, or even more.

For a contemplated embodiment of the current invention in which the post-specimen optic is a circularly symmetric polished dimple on the exit face 29 of the outer tube 32, and in which this post-specimen optic functions as a plano-concave diverging lens, the front focal plane of the lens is at infinity. There is no back focal plane. Thus, a magnified projection image, pseudoprojection image, or shadowgram containing information about the absorption of the illumination as it passed through the cell or other object to be imaged 1, can be produced by capturing this emergent pattern of transmitted light intensities on a TDI, CCD or CMOS detector or other digital imaging detector 39. The photo-conversion surface of the detector can be situated in any plane perpendicular to the system's optical axis and downstream from the post-specimen optic. Furthermore, the magnification can be chosen by the placement of the detector plane: the further the detector plane is downstream from the object, the greater the magnification.

Figure 4:
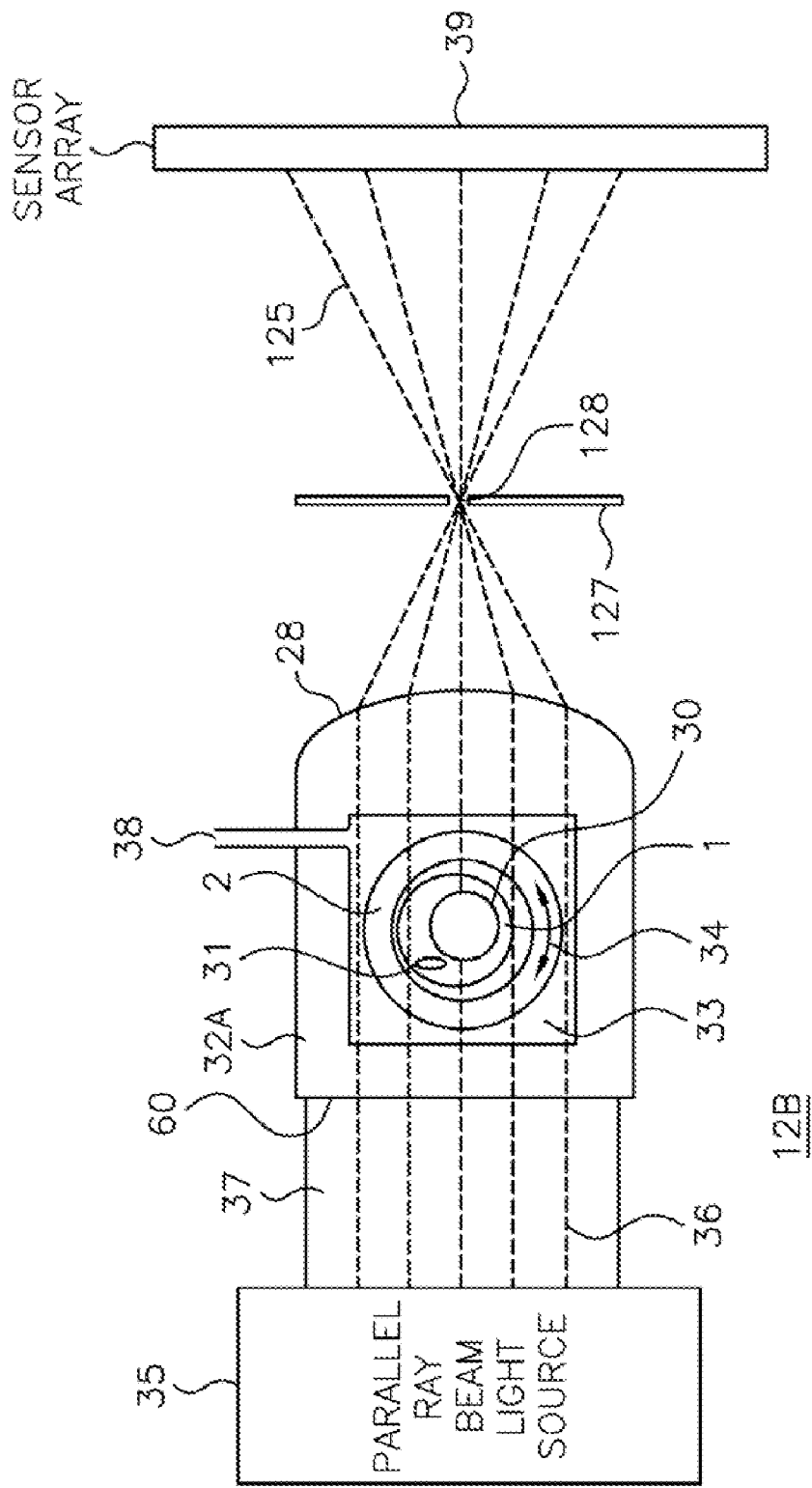
FIG. 4 schematically shows an example illustration of a system illumination geometry, including a single source-magnifying convex optic pair as contemplated by an alternate embodiment of the present invention.

In embodiments of the present invention such as those depicted schematically in FIG. 3 and FIG. 4, having a single source-detector pair, two-dimensional or three-dimensional tomographic imaging of the cell or other microscopic object is performed by obtaining images from varying angles of view. After obtaining a first projection with the object containing tube 2 held stationary at a first rotational angle with respect to the optical axis, the object containing tube 2 may be rotated by a discrete angle about an axis as indicated by the double arrow 34. A useful axis is identified as the Z axis in FIG. 2, and/or pointing out of the page in FIG. 3 and FIG. 4, that is perpendicular to the system's optical axis in order to orient the cell or other object 1 at a second rotational angle with respect to the optical axis. A subsequent transmitted projection image may be obtained after rotation of the object containing tube 2. The process of rotating and imaging may be repeated with the object containing tube 2 repeatedly rotated in discrete increments. A two-dimensional projection image is recorded at each angle until a sufficient number of projections are obtained to produce a three-dimensional image of the cell or other object 1, or portion thereof, or to produce two-dimensional images depicting slices of the absorption pattern in the imaged object's interior.

Three-dimensional reconstructions are produced by image processing of the plurality of two-dimensional projection images with known three-dimensional image reconstruction algorithms. Two-dimensional images of transverse slices through the imaged object are produced by processing lines of data extracted from the plurality of projections, where these lines of data are oriented parallel to rotated versions of the X and Y axes as depicted in FIG. 1 and FIG. 2. The lines of data are generally referred to as rows of detector data. The ability to reconstruct transaxial slices through the cell or other object from rows of detected projection data is an advantage of the method described in the present invention relative to cone beam geometry, in which many lines of detector data would contribute to each transverse image plane through object space.

Referring now to FIG. 4, there shown schematically is an alternate embodiment of a system illumination geometry within a reconstruction cylinder 12B as contemplated by the present invention, where a cell or other object to be imaged 1 may be present in a flow tube or entrainment tube 2. The reconstruction cylinder 12B includes a parallel ray beam radiation source 35 for illuminating the object of interest 1 with a plurality of parallel radiation beams 36. An outer tube 32A has an optically flat input surface 60 and a convex output surface 28, where the convex outer surface 28 focuses radiation emerging from the outer tube 32A after passing through the object of interest 1. As in the above embodiment described with respect to FIG. 3, an object containing tube 2 is located within the outer tube 32A, wherein the object of interest 1 is held within or flows through the object containing tube 2. A motor, indicated schematically by double arrow 34, may advantageously be coupled to rotate and/or translate the object containing tube 2 so as to present differing views of the object of interest 1. A pinhole aperture 127 is located at the focal point 128 of the convex lens and arranged to produce a cone beam of emergent radiation 125. As described above, a detector array 39 is located to receive the cone beam of emergent radiation 125 from the pinhole aperture 127. In one example embodiment, the outer tube 32A may advantageously have a port 38 and the space 33 around the object containing tube 2 is filled with a fluid such as optical oil having the same index of refraction as the outer tube 32A and the object containing tube 2.

Figure 4A:
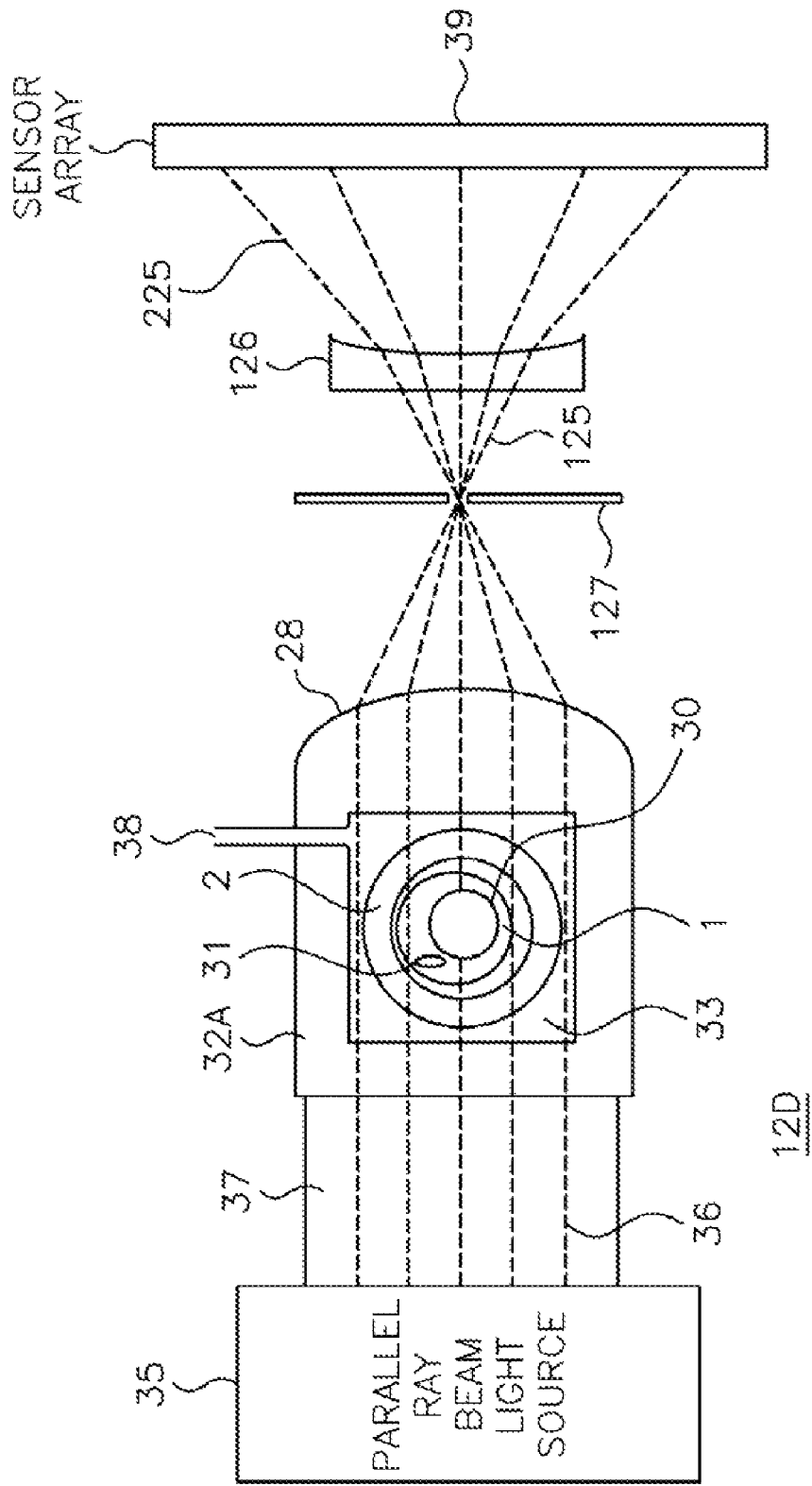
FIG. 4A schematically shows another example illustration of a system illumination geometry, including a single source-magnifying convex optic pair as contemplated by another alternate embodiment of the present invention.

Referring now to FIG. 4A, there shown schematically is another alternate embodiment of a system illumination geometry within a reconstruction cylinder 12D as contemplated by the present invention, where a cell or other object to be imaged 1 may be present in a flow tube or entrainment tube 2. The reconstruction cylinder 12D includes all of the elements as in the above embodiment described with respect to FIG. 4, with the addition of an optical element 126. The optical element 126 may advantageously comprise a plano-concave or other diverging or magnifying optic located between the pinhole aperture 127 and the sensor array 39. As in FIG. 4, a pinhole aperture 127 is located at the focal point 128 of the convex lens 28 and arranged to produce a cone beam of emergent radiation 125. The emergent radiation 125 is received by the plano-concave optical element 126, whereby it is further diverged into radiation beams 225. As described above, a detector array 39 is located to receive a cone beam of emergent radiation 225 from the pinhole aperture 127.

Figure 5:
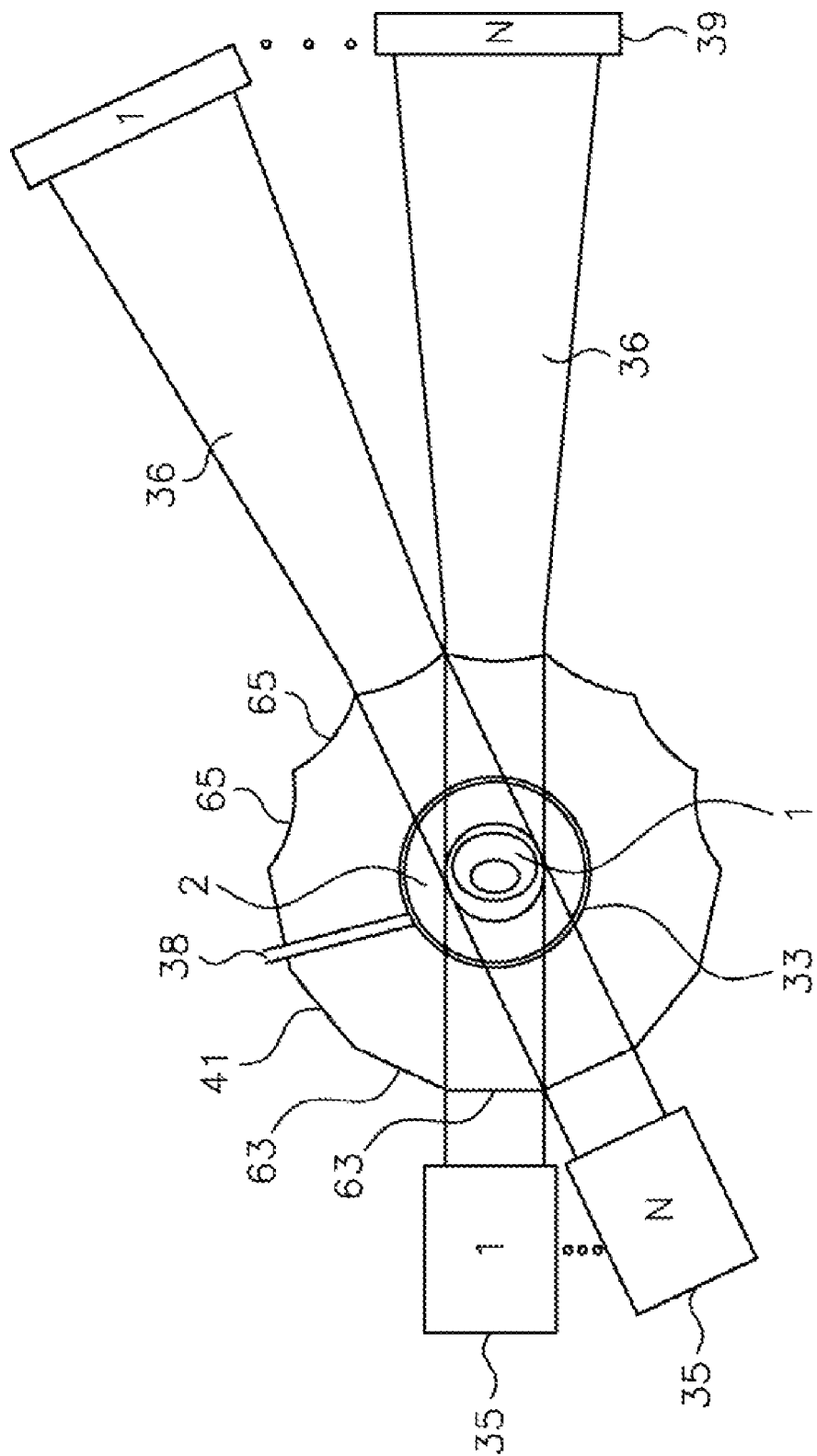
FIG. 5 schematically shows an example illustration of an illumination geometry and the imaged sample volume with multiple source-magnifying concave optic pairs as contemplated by an embodiment of the present invention.

FIG. 5 schematically shows an example illustration of illumination geometry and imaged sample volume with multiple source-magnifying concave optic pairs as contemplated by another embodiment of the present invention. A parallel-beam optical tomography system for imaging an object of interest 1 generally includes the illumination geometry described above with reference to FIG. 3 and a plurality of parallel ray beam radiation sources 1-N 35, where N is at least two, for illuminating the object of interest 1. Each of the plurality of parallel ray beam radiation sources 1-N 35 generates a plurality of parallel radiation beams at a differing angle of view with respect to the object of interest 1. Each of the plurality of parallel ray beam radiation sources 1-N 35 may be an individual light source, such as a laser, or at least one laser with light routed through one or more optical fibers or optical fiber bundles, as described herein below with respect to FIG. 8. An outer tube 41 has a plurality of optically flat input surfaces 63 and a plurality of corresponding concave output surfaces 65, where the plurality of corresponding concave output surfaces 65 cause the radiation emerging from the outer tube 41 to diverge after passing through the object of interest 1, so as to produce magnified projection images of the object 1. Alternatively, as described above with reference to FIG. 3, the post-specimen optic may comprise any magnifying optical element or combination of elements, including lens multiplets or other equivalents.

As in the other examples described herein, an object containing tube 2 is located within the outer tube 41 wherein the object of interest 1 is held within the object containing tube 2, and a plurality of detector arrays 1-N 39 are disposed to receive emerging radiation 36. Each of the plurality of detector arrays 1-N 39 is located to receive the emerging radiation 36 from one or more of the plurality of concave output surfaces 65.

Figure 5A:
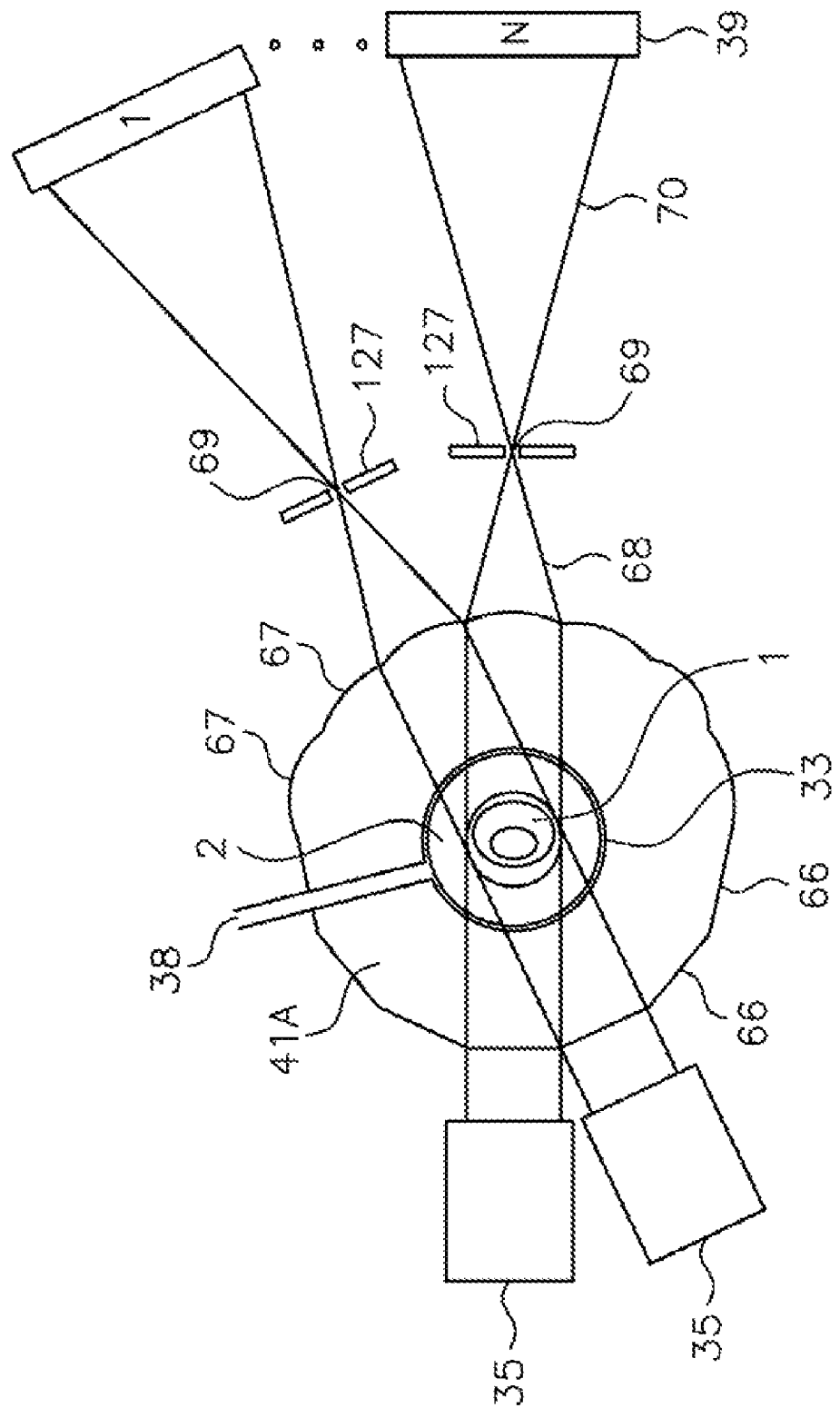
FIG. 5A schematically shows another example illustration of the illumination geometry and the imaged sample volume with multiple source-magnifying convex optic pairs as contemplated by an embodiment of the present invention.

FIG. 5A schematically shows another example illustration of illumination geometry and imaged sample volume with multiple source-magnifying convex optic pairs as contemplated by an embodiment of the present invention. FIG. 5A is constructed substantially similar to FIG. 5, with the exceptions that an outer tube 41A has a plurality of optically flat input surfaces 66 and a plurality of corresponding convex output surfaces 67, where the plurality of corresponding convex output surfaces 67 focus radiation 68 emerging from the outer tube 41A after passing through the object of interest 1. An object containing tube 2 is located within the outer tube 41A, wherein the object of interest 1 is held within the object containing tube 2. A plurality of pinhole apertures 127 are located at the respective focal points 69 of the convex output surfaces 67 where each of the plurality of pinhole apertures 127 receives radiation from one of the plurality of corresponding convex output surfaces 67 so as to produce an emergent cone beam 70.

A plurality of detector arrays 1-N 39 are disposed to receive the cone beams 70. Each of the plurality of detector arrays 1-N 39 is constructed as described hereinabove and located to receive the emerging radiation from one or more of the plurality of pinhole apertures 127.

Figure 6:
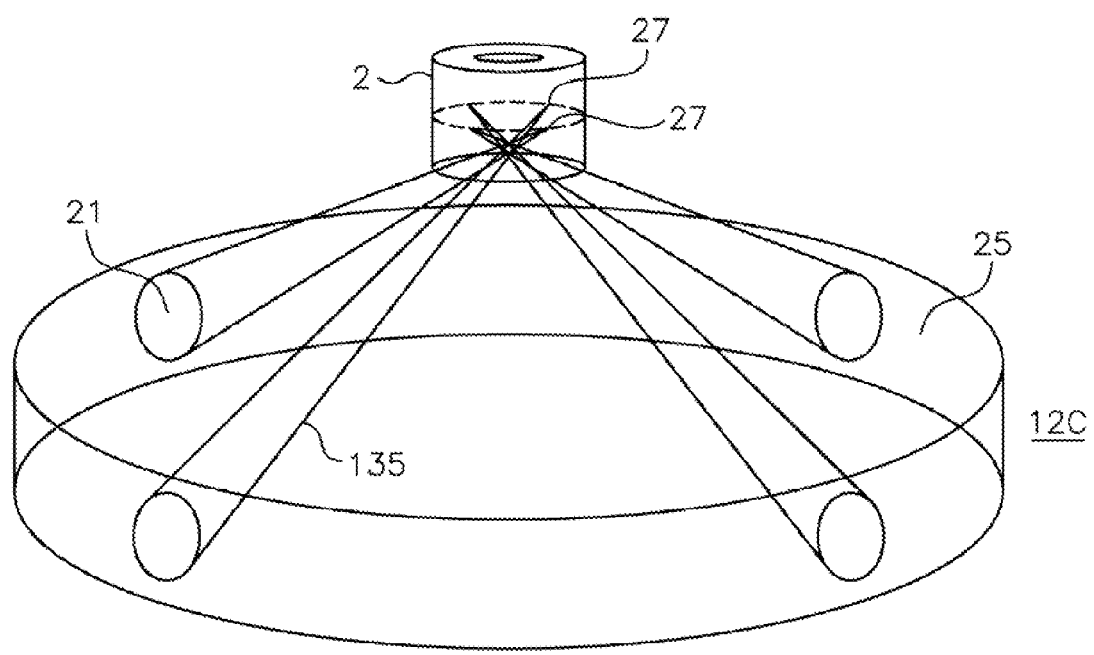
FIG. 6 is a highly schematic drawing that shows an example illustration of a reconstruction cylinder as contemplated by an embodiment of the present invention.

Referring to FIG. 6, there shown is a useful design of a reconstruction cylinder 12C as contemplated by an embodiment of this invention. Here, a ring of point sources 27 is disposed about the object containing tube 2 and a ring of image sensors 25 is placed in a plane situated above, at or below the plane containing the point sources 27. While only four point sources and four sensors are shown in the illustration, it will be understood that the rings of sources and image sensors may advantageously comprise a greater number, that being enough to enable tomographic reconstruction of imaged objects. The image sensors can be below or above or in the plane of the point sources. By placing the point sources 27 and image sensors 25 on separate planes, point sources on opposing sides of the cylinder will not physically interfere with other illumination beams. Each of the point sources may advantageously generate a parallel ray beam 135 which may be magnified after passing through the imaged object as described herein above with reference to FIGS. 3, 4, 4A, 5 and 5A.

During the course of moving through the reconstruction cylinder, the cell 1 passes through at least one photon point source. A central feature of the present invention is that a number of photon point sources 27 of selectable wavelength are disposed around and concentric with the object containing tube. The photon point sources operate in conjunction with opposing CCD, CMOS, TDI or other image sensors 25 that are sensitive to selectable portions of the light spectrum, thus allowing the acquisition of projections 21 of the light transmitted through the cell 1. In this manner, a set of projection rays 135 can be generated where the projection rays can be described as the straight line connecting the source point to an individual sensing element. The difference between the number of photons leaving the source point along a particular projection ray and the number of photons received at the particular sensing element is related to the number of photons lost or attenuated due to interactions with the cell and other contents of the object containing tube 2 along the projection ray path.

However, complications may arise from light scatter, photon energy shifts, imperfect geometry and poor collimation, and photons from different sources may arrive at a particular sensing element when multiple source points are energized simultaneously. With careful construction of the reconstruction cylinder, for example by judicious choice of the geometry for the pattern of point sources and their opposing detectors as described herein, and by proper timing or multiplexing of activation of the multiple point sources and readout of the sensor arrays, the photon contamination due to these issues can be minimized.

Photon contamination can be partially accounted for by calibration of the system, for example, with no cells present. That is, each light source may be illuminated in turn and its effects on each of the sensors can be measured, thereby providing offset data for use in normalizing the system. An additional calibration step may entail, for example, imaging latex polymer beads or other microspheres or oblate spheroids whose optical properties are known and span the density range of interest for cellular imaging.

Figure 7:
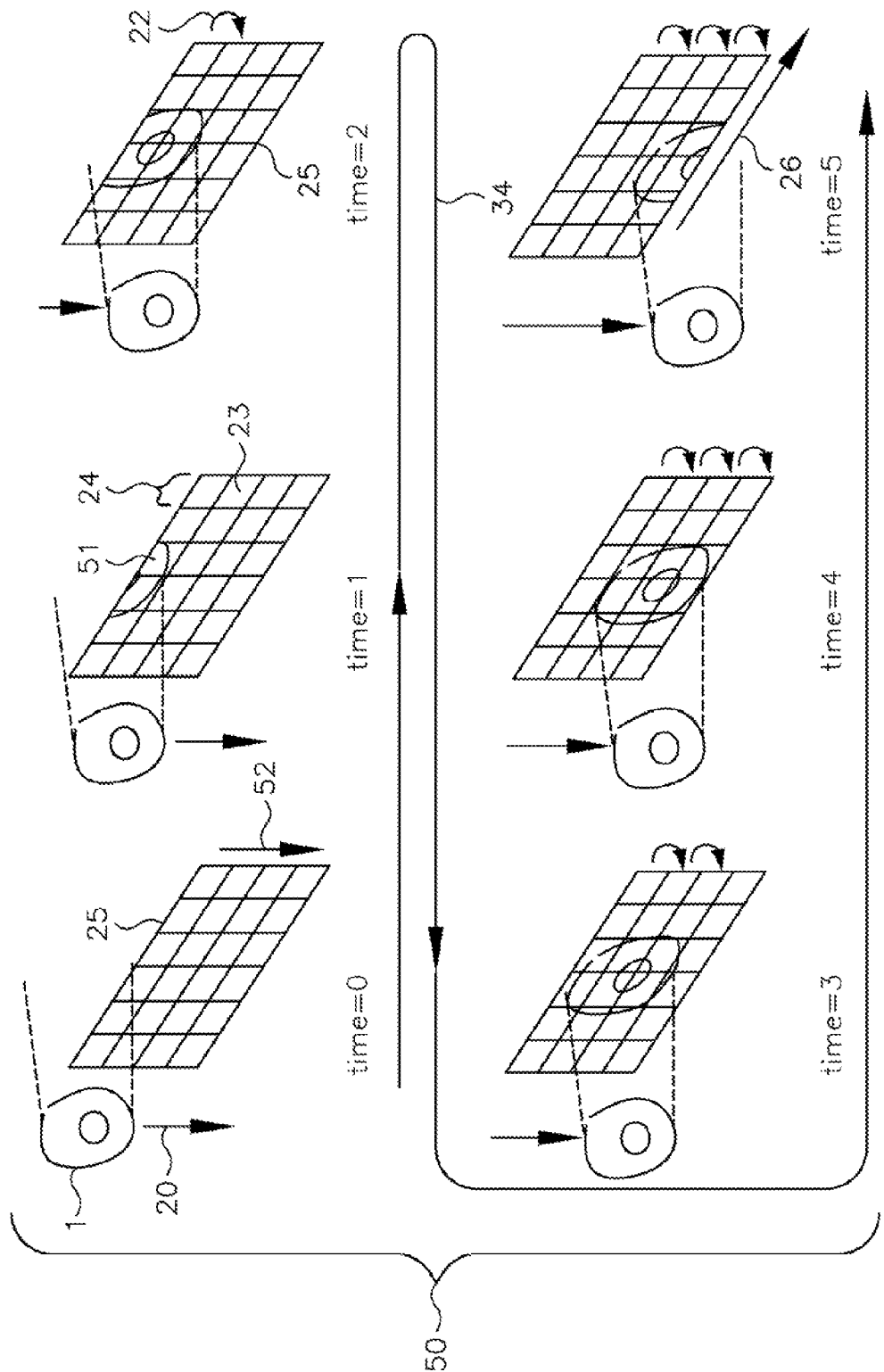
FIG. 7 schematically shows an example flow diagram illustrating the operation of a TDI image sensor as contemplated by an embodiment of the present invention.

Now referring to FIG. 7, there schematically shown is an example of a flow diagram 50 illustrating the operation of a TDI image sensor. Charge corresponding to an image element of the cell is transferred down a column of pixel elements 51 of the TDI sensor in synchrony with the image. The charge transfer occurs sequentially until the accumulated charge from the column is read out at the bottom register of the sensor 26.

In one embodiment of the optical tomography system contemplated by the invention, a plurality of TDI sensors 25 are oriented such that each sensor has a direction of line transfer 52 that is parallel to that of cell movement 20 along the z-axis. The TDI image sensor line transfer rate is synchronized to the velocity of the cells by timing or clocking signals from the computer 13.

The flow diagram of FIG. 7 shows a moving cell 1 and its location with respect to a TDI sensor 25 at various times along a time line 34. At time=0 the cell 1 is just above the TDI sensor 25 and no image is sensed. At time=1 the cell 1 is partially imaged by the TDI sensor 25. A shadowgram 51 of the cell 1 is imaged one line at a time. Electrical charges 22 corresponding to each image line are transferred to the next line of sensor pixel elements 23 in synchrony with the movement of that image line down the TDI image sensor from time=0 to time=5. In this way, electrical charge corresponding to each pixel is accumulated down each column 24 of the TDI detector 25 until it is read out at the bottom register 26 at time=5.

The TDI sensors are oriented such that the direction of line transfer 52 is the parallel to that of cell movement 20 along the z-axis. The TDI image sensor line transfer rate is synchronized to the velocity of the cells. Depending on the number of lines or stages in the TDI image sensor, additional photogenerated charge is accumulated and the signal is boosted (e.g., up to 96 fold with a 96 stage TDI sensor such as the Dalsa IL-E2 sensor).

Light Source.

Figure 8:
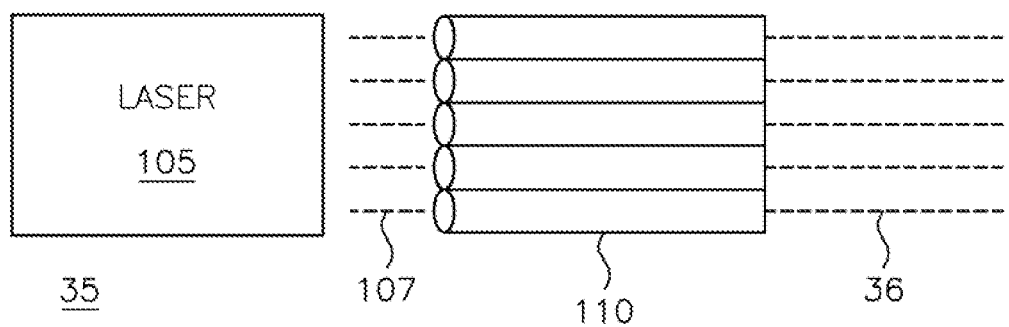
FIG. 8 schematically shows an example illustration of a parallel ray beam light source system as contemplated by an embodiment of the present invention.

Referring now to FIG. 8, an example illustration of a parallel ray beam light source as contemplated by an embodiment of the present invention is schematically shown. In this example, the parallel ray beam light source includes a laser 105 coupled to optical fibers 110. The optical fibers 110 may comprise individual fibers or optical fiber bundles or the equivalent. In operation the plurality of optical fibers 110 receive laser beams 107 and deliver parallel radiation beams 36 to source positions surrounding the flow tube or capillary tube. In this way, the number of lasers needed for multiple light source systems, such as, for example, described with respect to FIG. 5 and FIG. 5A above, may advantageously be reduced by routing light beams from a single laser through a number of optical fibers. Optical elements such as lenses and/or mirrors may be incorporated at the input or output, or both, of the optical fibers 110.

In operation, each laser beam diameter may be on the order of one-half to several millimeters, allowing a single laser to couple many optical fibers having openings ranging from about thirty microns to one hundred-micron fibers out of each laser source.

Each source may have the same general characteristics, preferably:
   it may approximate a small circular point source,
   it may be a laser, laser diode or light emitting diode,
   it may be bright with known spectral content,
   the photons emitted from the source may form a beam of a known geometry such as a pencil beam where all photon rays are parallel.

Each source creates data for one projection angle. In an example data collection geometry, a plurality of sources arranged along a helix whose axis is the center axis of the object containing tube creates data from multiple projection angles as the cell moves through the module. Depending on the sensor geometry, several point sources could be disposed about the same circumference with angular separation such that the projections do not overlap at the sensor. The desired number of sources is a function of the needed resolution within each planar reconstruction (the x-y plane) or volumetric reconstruction. Further, the wavelength of the sources is selectable either by use of various diode or other lasers or by bandpass filtering of a white or other broadband source, for example a mercury or xenon arc lamp. There are several options that can be employed to create optical source points, such as:
   a laser or laser diode,
   a laser-fiber bundle combination,
   an aperture in front of a laser or other high intensity photon source,
   an aperture utilizing surface plasmon focusing of photons on both the entry and exit sides of the pinhole,
   an optical fiber with a small cross-section,
   a virtual point source from a short focal length lens in front of a photon source,
   an electron beam that irradiates a point on a phosphor surface (a form of CRT), and
   various combinations of the above.

The geometry using a diverging beam of light is such that, the closer the point source to the object of interest 1 (e.g. a cell), the higher the magnification due to the wider geometric angle that is subtended by an object closer to the source. Magnification in a simple projection system is approximately $M=(A+B)/A$, where A is the distance between the point source and the object (cell) and B is the distance between the object and the detector. Conversely, if the required resolution is known in advance of the system design, then the geometry can be optimized for that particular resolution. For background, those skilled in the art are directed to Blass, M., editor-in-chief, *Handbook of Optics: Fiber Optics and Nonlinear Optics*, $2^{nd}$ ed., Vol. IV, Mcgraw-Hill, 2001.

Figure 9:
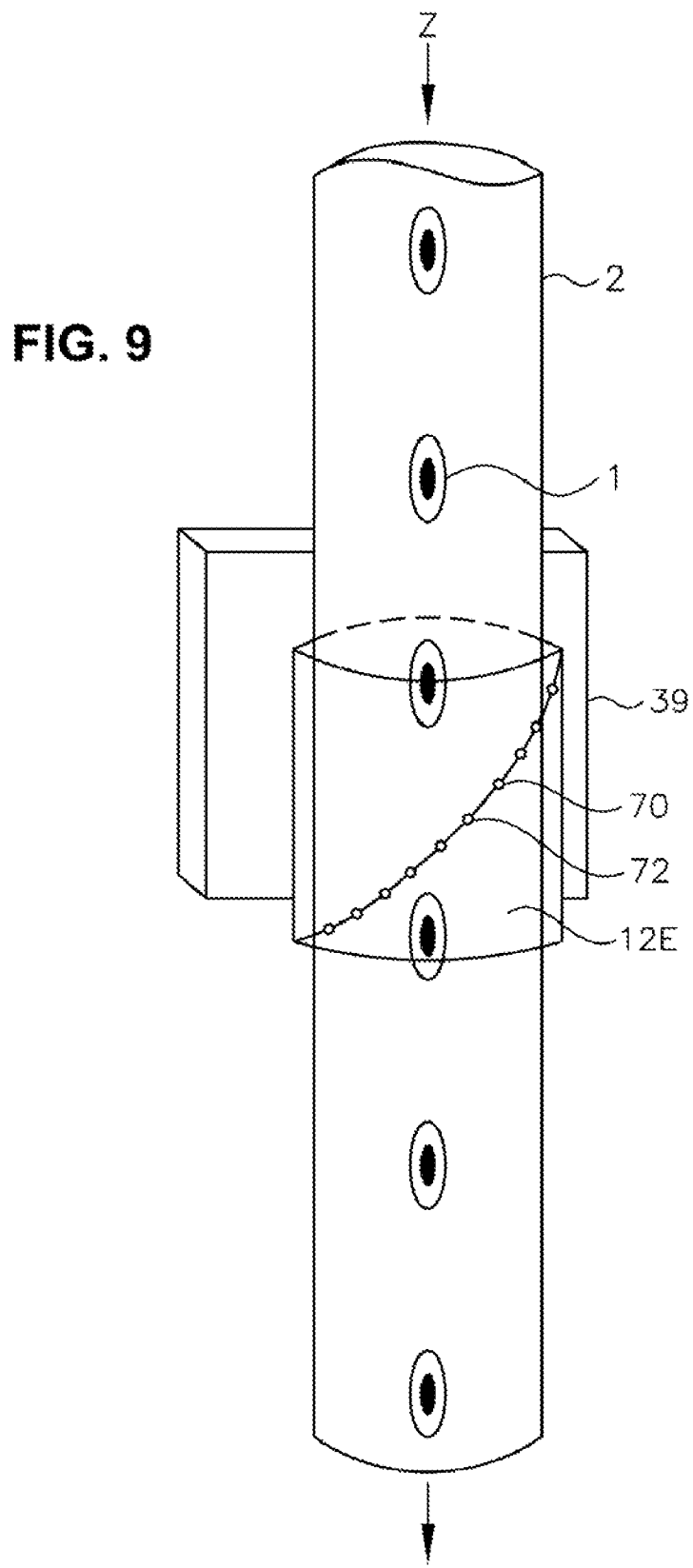
FIG. 9 schematically shows an example of a reconstruction cylinder surrounding a flow tube containing flowing object, such as cells, as contemplated by an embodiment of the present invention.

Referring now to FIG. 9, there shown schematically is an example of a reconstruction cylinder 12E, surrounding flow tube 2 containing flowing objects 1, such as cells, as contemplated by an embodiment of the present invention. A reconstruction cylinder 12E includes, for example, a helix 70 including a plurality of parallel ray beam sources 72 disposed at a predetermined helical pitch. Sensing elements 39 are disposed to receive light from the point sources, after it passes through the cell or other object of interest 1 and is magnified by post-specimen optical elements as described above with reference to FIGS. 3, 4, 4A, 5 and 5A.

While the arrangement of the plurality of parallel ray beam sources 72 is helical, an array of parallel ray beam sources used in a reconstruction cylinder as contemplated by the present invention may take on a wide variety of geometric patterns, depending in part on the speed of the electronics, the cell velocity and the geometry that achieves non-overlapping projection signals at the sensor (detector).

Figure 10:
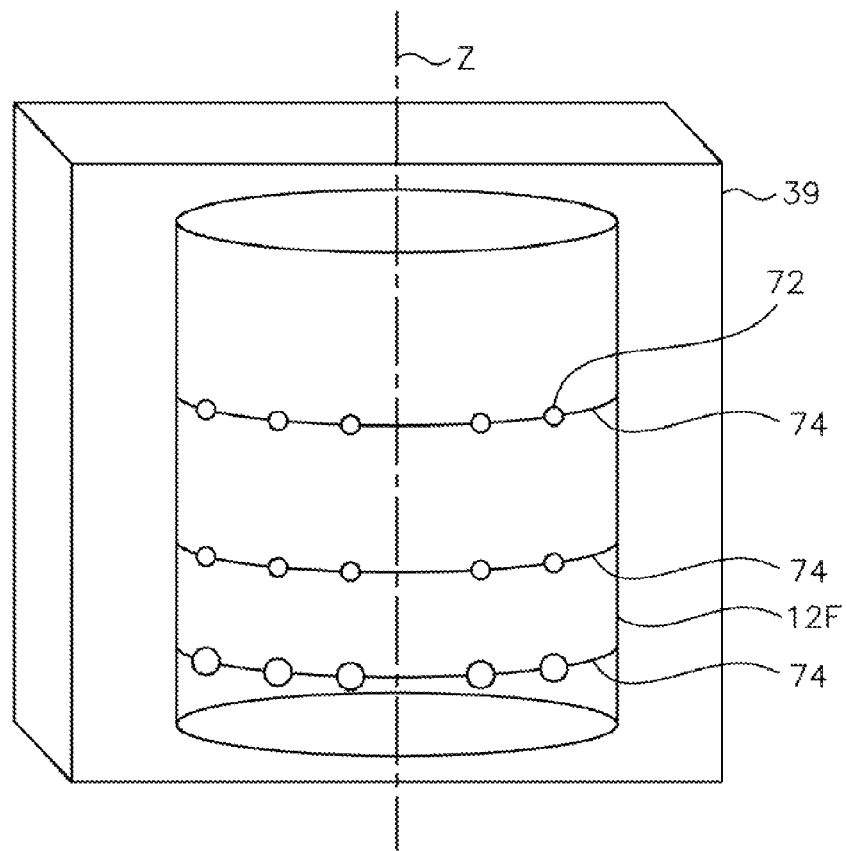
FIG. 10 schematically shows an example of a reconstruction cylinder including a series of partial circumferences arranged along a Z-axis through an object containing tube, wherein each partial circumference may contain more than one source-detector pair.

For example, with reference to FIG. 10, there shown is a reconstruction cylinder 12F including a series of partial circumferences 74 arranged along a Z-axis through the object containing tube 2, wherein each partial circumference 74 may contain more than one source-detector pair.

The fixed optical point sources 72, in conjunction with opposing detectors 39 mounted around a circumference of the tube can sample multiple projection angles through the entire cell as it flows past the sources. By timing of the emission or readout, or both, of the light source and attenuated transmitted and/or scattered and/or emitted light, each detected signal will coincide with a specific, known position along the axis in the z-direction of the flowing cell. In this manner, a cell flowing with known velocity along a known axis perpendicular to a light source that is caused to emit or be detected in a synchronized fashion can be optically sectioned with projections through the cell that can be reconstructed to form a 2D slice in the x-y plane. By stacking or mathematically combining sequential slices, a 3D picture of the cell will emerge. It is also possible to combine the cell motion with the positioning of the light source (or sources) around the flow axis to generate data that can be reconstructed, for example, in a helical manner to create a 3D picture of the cell. Three dimensional reconstruction can be done either by stacking contiguous planar images reconstructed from linear (1D) projections, or from planar (2D) projections directly. The 3D picture of the cell can yield quantitative measures of sub-cellular structures and the location and amount of tagged molecular probes that provide diagnostic information.

Focal Plane and Object Tracking

An optical tomography system for imaging an object of interest is further contemplated by the invention as described herein. The optical tomography system includes a light source for illuminating the object of interest with a plurality of radiation beams, an object containing tube, wherein the object of interest is held within the object containing tube such that it is illuminated by the plurality of radiation beams to produce emerging radiation from the object containing tube. A detector array located to receive the emerging radiation and produce imaging data. Means for tracking the object of interest is coupled to receive and respond to the imaging data.

The image of the object of interest may comprise a projection image or a pseudoprojection image. A pseudoprojection image is typically produced by integrating a series of images from a series of focal planes integrated along an optical axis. The focal planes are preferable arranged back-to-back. The tracking means as described herein may include means for tracking a pseudoprojection image center, means for tracking a projection image center, or means for tracking a focal plane.

Figure 11:
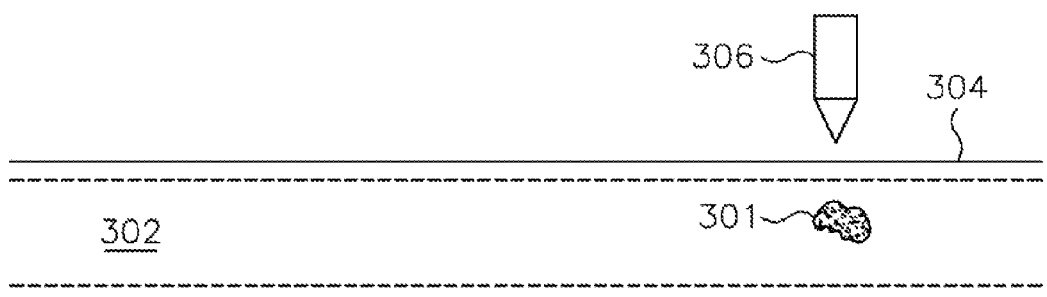
FIG. 11 schematically shows another example embodiment of the system and method wherein at least one specimen for examination is processed to remove non-diagnostic elements and is fixed and stained as contemplated by an embodiment of the present invention.

Referring now to FIG. 11, there shown is another example embodiment of the shadowgram optical tomography system of the invention wherein at least one specimen 301 for examination, as for example, a cell or plurality of cells, is processed to remove non-diagnostic elements and is fixed and stained. The specimen 301 is then suspended in a gel medium 302. The cells in gel mixture are then inserted into a glass micro-capillary tube 304 of approximately 40 µm-60 µm inner diameter. In one implementation, pressure is applied to the gel to move a specimen 301 into the optical path of a high-magnification microscope, represented here by objective 306. In an alternative embodiment, the tube may be translated relatively to the objective while the specimen remains stationary relatively to the tube.

Once the specimens are in place the tube 304 is rotated to permit capture of a plurality of high resolution images of the desired object taken over a predetermined range of tube rotation. In one useful embodiment about 250 images are obtained over a tube rotation range of 180 degrees. When integrated along the optical axis the images form a pseudoprojection image. The images are typically processed using filtered back projection to yield a 3-D tomographic representation of the specimen. Based on the tomographic reconstruction, features may be computed and used to detect cells with the characteristics of cancer and its precursors. These features are used in a classifier whose output designates the likelihood that object under investigate is a cancer cell. Among other things, good quality reconstruction and classification depends on good focus for all images taken in step three. The present invention provides a method to establish good focus across all pseudoprojections taken during processing as described herein.

Figure 12A:
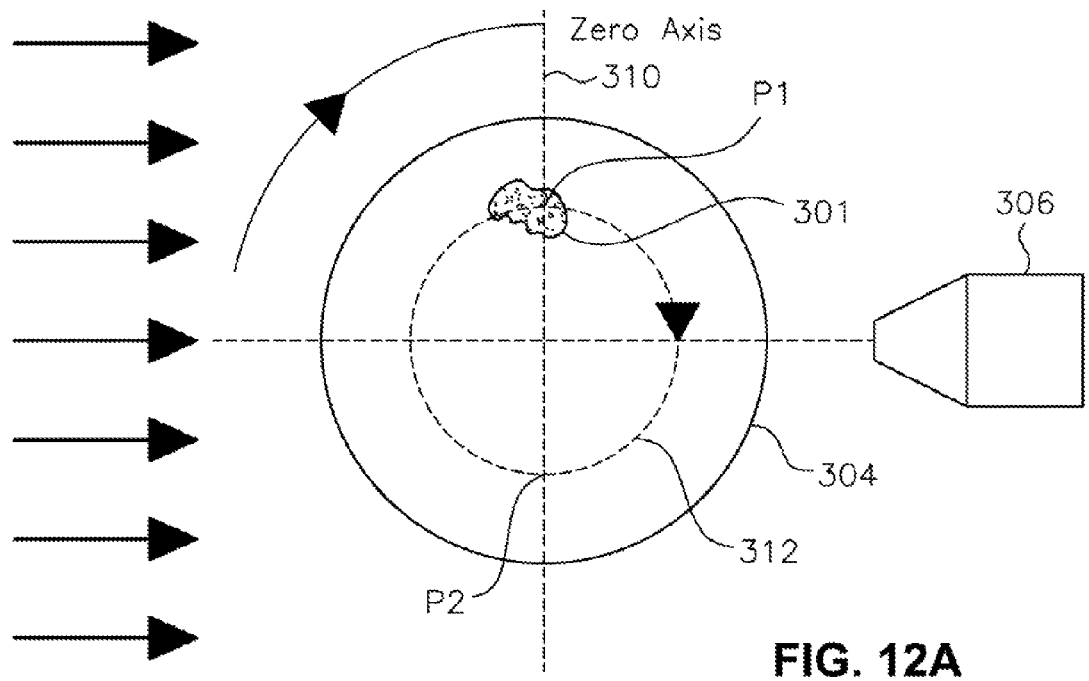
FIG. 12A and FIG. 12B schematically show an end view of a micro-capillary tube 304 with parallel beam illumination and non-parallel beam illumination respectively.
Figure 12B:
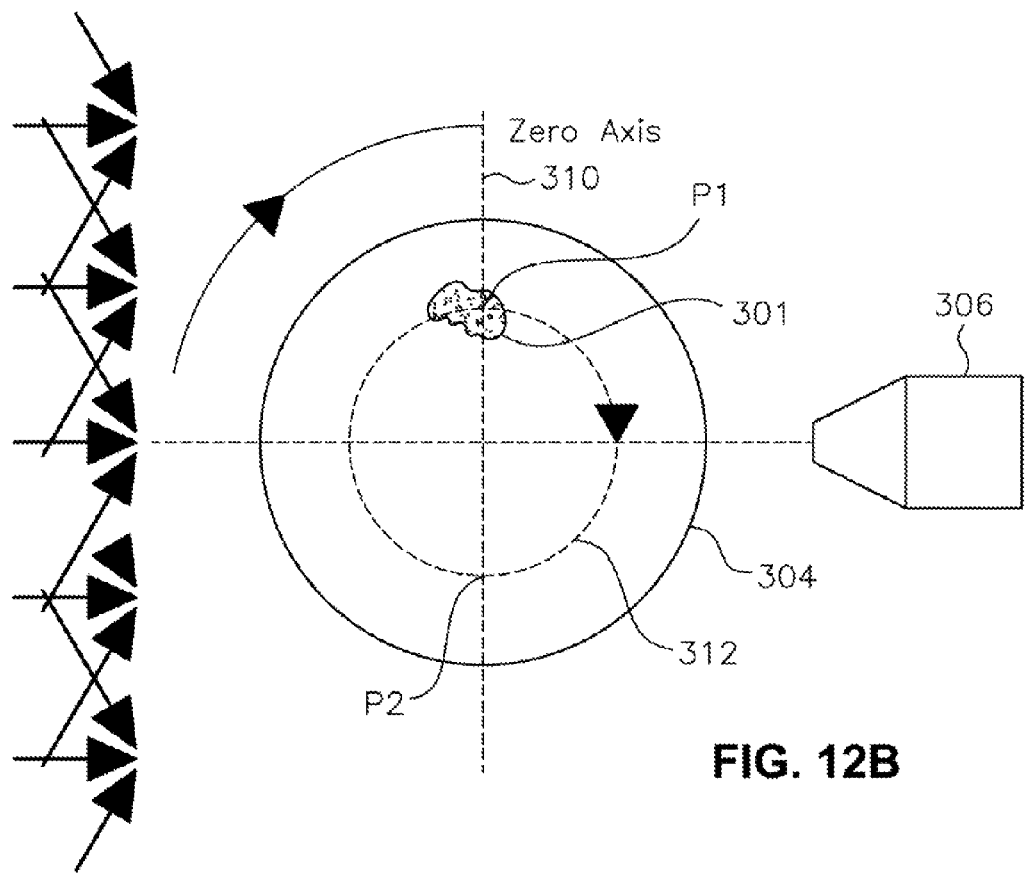

Referring now to FIG. 12A and FIG. 12B, an end view of a micro-capillary tube 304 is shown with parallel beam illumination and non-parallel beam illumination respectively. In either case, to minimize diffraction of light after it has left an object of interest, such as specimen 301, it is advantageous to turn the tube so as to minimize the distance between the object and the objective lens, integrated over the duration of an image capture cycle. Thus the image capture must be initiated when the object of interest, specimen 301, is at position P1 located within zero axis 310, where the zero axis 310 runs transverse to and preferably perpendicular to the optical axis of the objective 306. The object of interest is then rotated as shown by the dashed line indicating the path of travel 312, and end at position P2. Note that in so doing the plane of focus for the system must be varied to correspond to the path of travel 312.

In one useful embodiment, a focal tracking system incorporated into the optical tomography system and method of the invention and operates to trigger capture of pseudoprojection images when the object center is aligned with the zero axis 310. The focal tracking system also operates to adjust the focus so that it tracks the object center as it rotates around the tube. Note that the tracking system as described herein may be employed in an optical tomography system that uses any suitable form of illumination or optics, including parallel beam illumination or optics, fan beam, point light sources and other equivalent light sources known to those skilled in the art.

Figure 13:
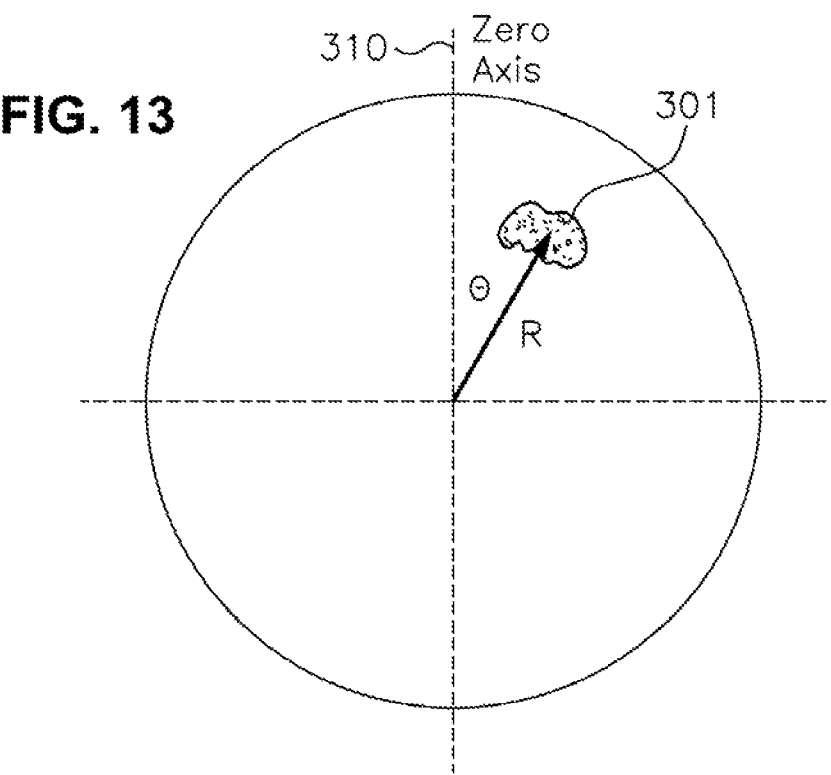
FIG. 13 schematically shows an example illustration of tracking parameters describing the placement of the object in a tube as contemplated by one example embodiment of the present invention.

Referring now to FIG. 13, tracking parameters describing the placement of the object in the tube are schematically shown, including:

R—The Radius from the tube center to the object center.
  Θ—Theta, the angular placement of the object relative to the 0 degree axis or angular error value when measured at initiation of image capture. (Image capture is most preferably initiated when Θ is 0, so any other value at initiation of image capture is an indication of angular error.)

Figure 14:
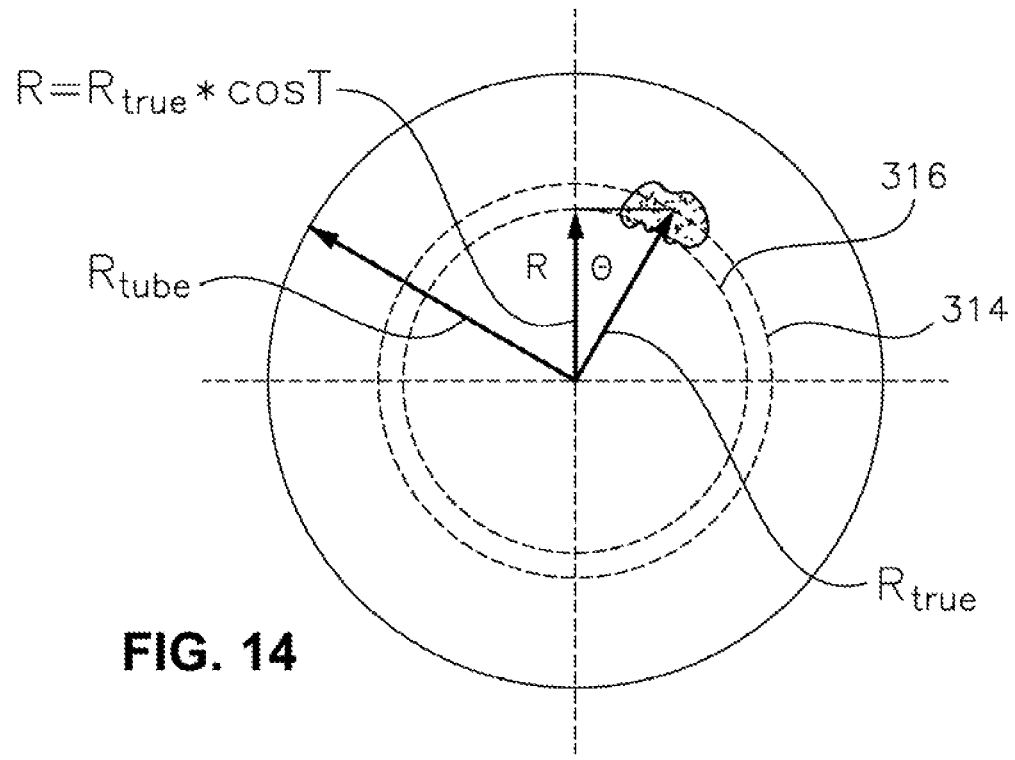
FIG. 14 schematically shows an example illustration of errors in a diagram that characterizes the erroneous identification of R, Θ resulting in a misidentification of the plane of focus for the object of interest.

Referring now to FIG. 14, errors are schematically illustrated in a diagram that characterizes the erroneous identification of R, Θ resulting in a misidentification of the plane of focus for the object of interest. Since the object travels on a circular path, image capture should be initiated with R correctly identified to the object center and when the object center is aligned with the zero axis. Errors arise when the object is assumed to be positioned on the zero axis, but is actually offset from the zero axis by Θ. Where Θ is other than zero (0), there is a difference between the true path of travel 314 for the object and the assumed path of travel 316. In such cases, R is also undervalued as indicated by the relationship $R=R_{true}\cos(\Theta)$. Although at the point when image capture is initiated the object is in focus, if no adjustment is made for the Θ offset as the object is rotated through 180°, an increasing error develops between the object center and the focal plane assigned by the tracking system.

The plane of focus F for the object may be modeled as:

$$F = F_{tube\ center} - R_{true} \cos(\Theta) \sin(\pi PP/249) \text{ where } PP \text{ is the image number:} \quad \text{Equation 1}$$

PP=0, 1, 2, . . . , 249

This path corresponds to the true and desired path of the object when R is the true value ($R_{true}$) and Θ=0. This trajectory may be modeled as in eqn. 2.

$$F_{true} = F_{tube\ center} - R_{true} \sin(\pi PP/249) \quad \text{Equation 2}$$

The error in focus $F_{error}$ may be modeled as the difference ($F - F_{true}$) using eqns. 1 & 2.

$$F_{error} = R_{true} \sin(\pi PP/249)(1 - \cos(\Theta)) \quad \text{Equation 3}$$

A metric for assessing the overall severity of the focus error may be found by integrating eqn. 3 over all PP.

$$F_{AllError} = (2\pi * R_{true}/249) * (1 - \cos(\Theta)) \quad \text{Equation 4}$$

Figure 15:
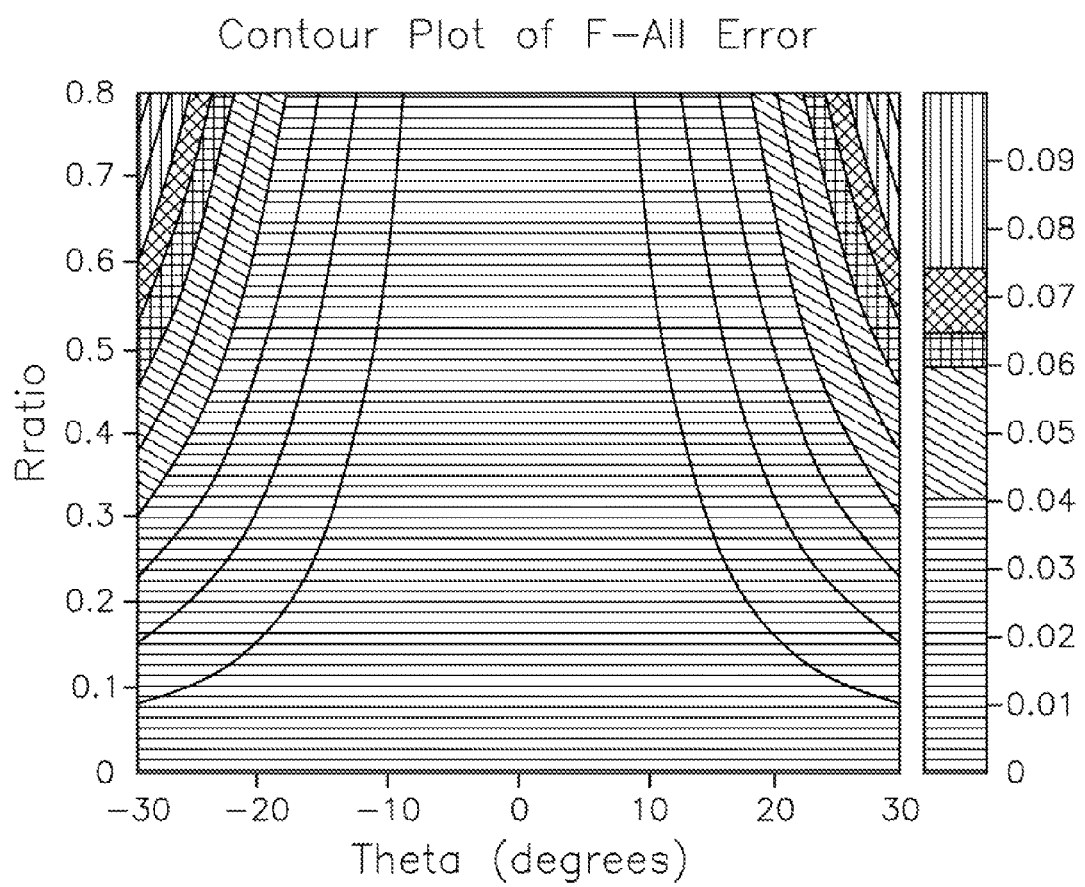
FIG. 15 schematically shows a contour plot representative of the dependence of F_AllError on Rratio and Θ as contemplated by another alternate embodiment of the present invention.

Taking $R_{true}/R_{tube} = R_{ratio}$, the second half of this equation is represented as a contour plot over $-30° \leq \Theta \leq 30°$ and $0 \leq R_{ratio} \leq 0.8$. This is represented in FIG. 15 and gives a sense for the dependence of $F_{AllError}$ on $R_{ratio}$ and Θ. Note that for the purposes of this example 249 represents the case where 250 pseudoprojection images are acquired. If a different number of pseudoprojection images are acquired the constant 249 must be adjusted accordingly.

Estimation of R, Θ by visual examination is an error prone enterprise since a fairly large Θ error is needed before an appreciable translation of the object is observed. On the other hand it can be difficult to render the distance to the true object center without certainty in Θ. Therefore it is the aim of the present invention to provide a method for 1. estimating R, and
2. establishing a means to trigger image capture so that data is taken as the object center passes through the zero axis 310.

Figure 16:
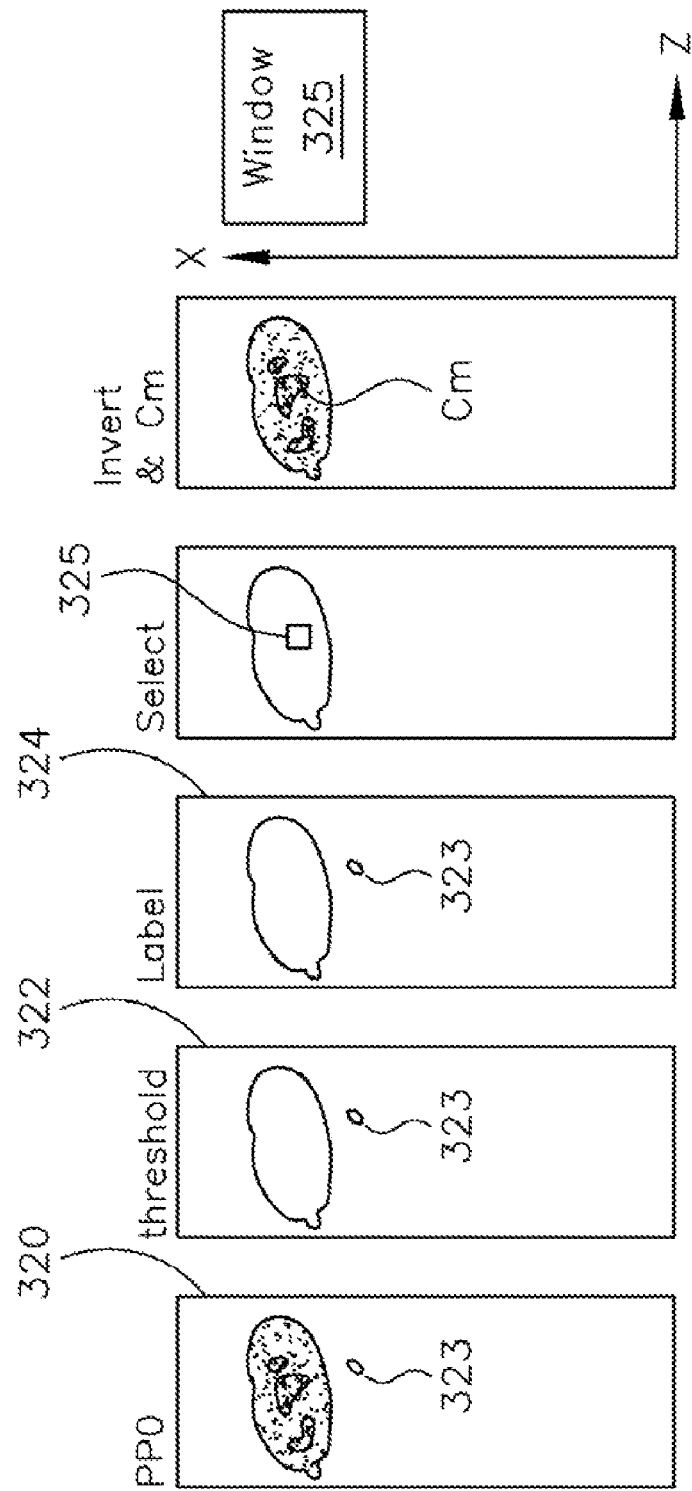
FIG. 16 schematically shows a diagram for segmenting an object of interest and computing the center of mass for the grey scale pixels associated with a pseudoprojection image PP0 of an object of interest is shown as contemplated by an embodiment of the present invention.

Referring now to FIG. 16, a diagram for segmenting the object of interest and computing the center of mass for the grey scale pixels associated with the a pseudoprojection image PP0 of an object of interest is shown. The first thing needed to estimate R is to find the object center of mass. This is accomplished by segmenting the object of interest and computing the center of mass for the grey scale pixels associated with the object of interest.

1. Threshold: A threshold for the pseudoprojection PP0 is found by finding the average light level in box region 320.
2. A connected components algorithm is applied to the thresholded image 322 in order to segment objects where all non-zero pixels are connected. This process yields the labeled image 324. Note that extraneous non-connected features, as for example feature 323, have been substantially removed and/or darkened by the threshold and connected components algorithms.
3. The component corresponding to the object of interest is selected based on identifying a pixel 325 in the object of interest.
4. Selection of the object 326 yields a mask that is then applied to the original grey value image. The object center is found by computing the center of mass $C_m$ based on inverted grey values.

In one example embodiment, the average light level is determined by measuring an average light level using a box region including the first 75 pixels from the top left corner moving down 75 pixels and over to the opposite edge. The threshold is set at approximately 85% of the average grey value of the pixels in the box region. Of course the invention is not so limited and those skilled in the art may use equivalent threshold-setting methods.

The step of selecting the object of interest may be based on a user input, for example, a user activating a pixel on a computer display screen or automatically with pattern recognition algorithms or equivalent software algorithms. Once the object of interest has been selected during acquisition of the first pseudoprojection, a window 325 through the capillary tube may be established, where the window is made larger than the object of interest in order to provide a view of the entire object, but not the part of the image containing uninteresting information. Then, during subsequent image acquisitions, it is only necessary to view the object through the window and the selection step can be skipped.

Figure 17:
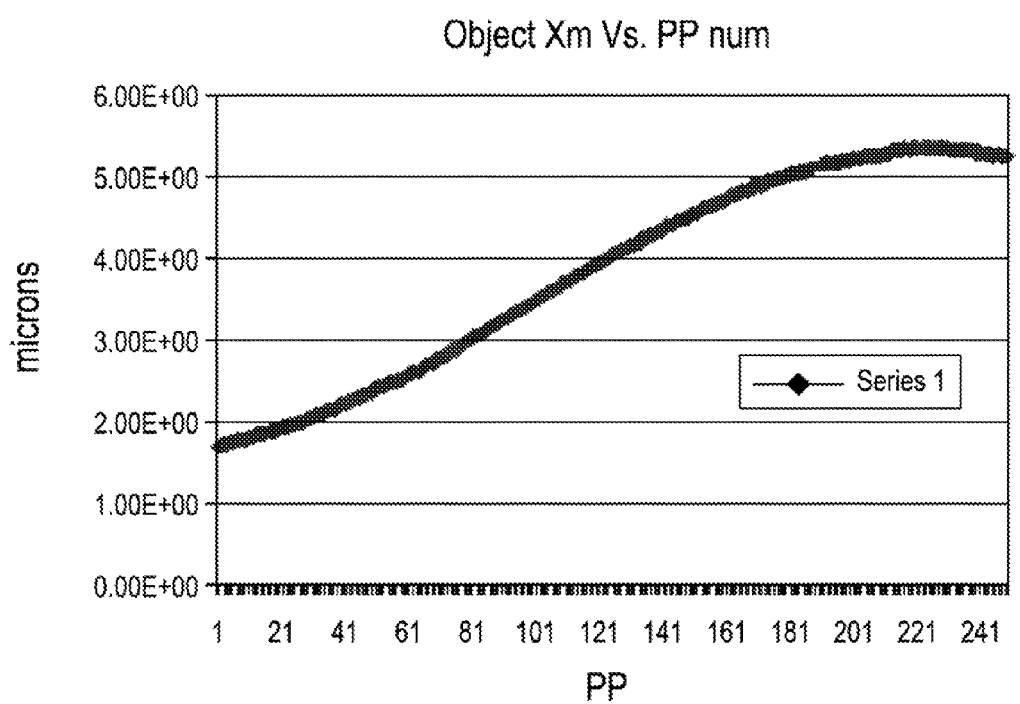
FIG. 17 schematically shows a graphical representation of a trend of an X component of the center of mass from pseudoprojection to pseudoprojection as contemplated by an embodiment of the present invention.

Referring now to FIG. 17, a graphical representation of the trend of X component of the center of mass from pseudoprojection to pseudoprojection is shown. The center of mass for a single pseudoprojection image is found as according to the method described hereinabove. Computing R and the Θ of the object, at the time image capture is initiated, may be made by analyzing the trend in the X component of the center of mass $X_m$ from pseudoprojection to pseudoprojection. Since the path of movement of the object is circular the translation of the object center with rotation may be described by a cosine function when the movement is viewed from the perspective of the objective lens.

The trend in $X_m$ data may be modeled as $X'_m$:

$$X'_m = R * \cos(\pi PP(1+\zeta)/249 + \pi + \Theta) + 34.7 + A + B*PP + C*PP^2 \quad \text{Equation 5}$$

In Eqn. 5 the parameters of the model have the significance as shown in Table 1.

TABLE 1

Model Parameter Descriptions

| Model Parameter | Description |
| --- | --- |
| R | Distance between the micro-capillary tube center and object center |
| Θ | Angular error |
| ζ | Controller error. ζ will be a value other than 0 when the controller rotates the object of through some other value than 180° |
| PP | Pseudoprojection Number: 0,1, . . . ,249 |
| 34.7 | Half of the pseudoprojection frame height in microns. The micro-capillary tube walls should be centered about this value. |
| A | The average offset (all PP) of the micro capillary tube around the tube center |
| B | The linear translation of the micro-capillary tube as it rotates |
| C | The second order translation of the micro-capillary tube as it rotates. |

Focal Track Parameter Solution

The parameters of Table 1 may be solved for by minimizing the RMS error between the $X_m$ and $X'_m$ for all 250 pseudoprojections in accordance with the following equation.

$$\text{Error} = \sqrt{\Sigma(X_m - X'_m)^2}/250 \quad \text{Equation 6}$$

Figure 18:
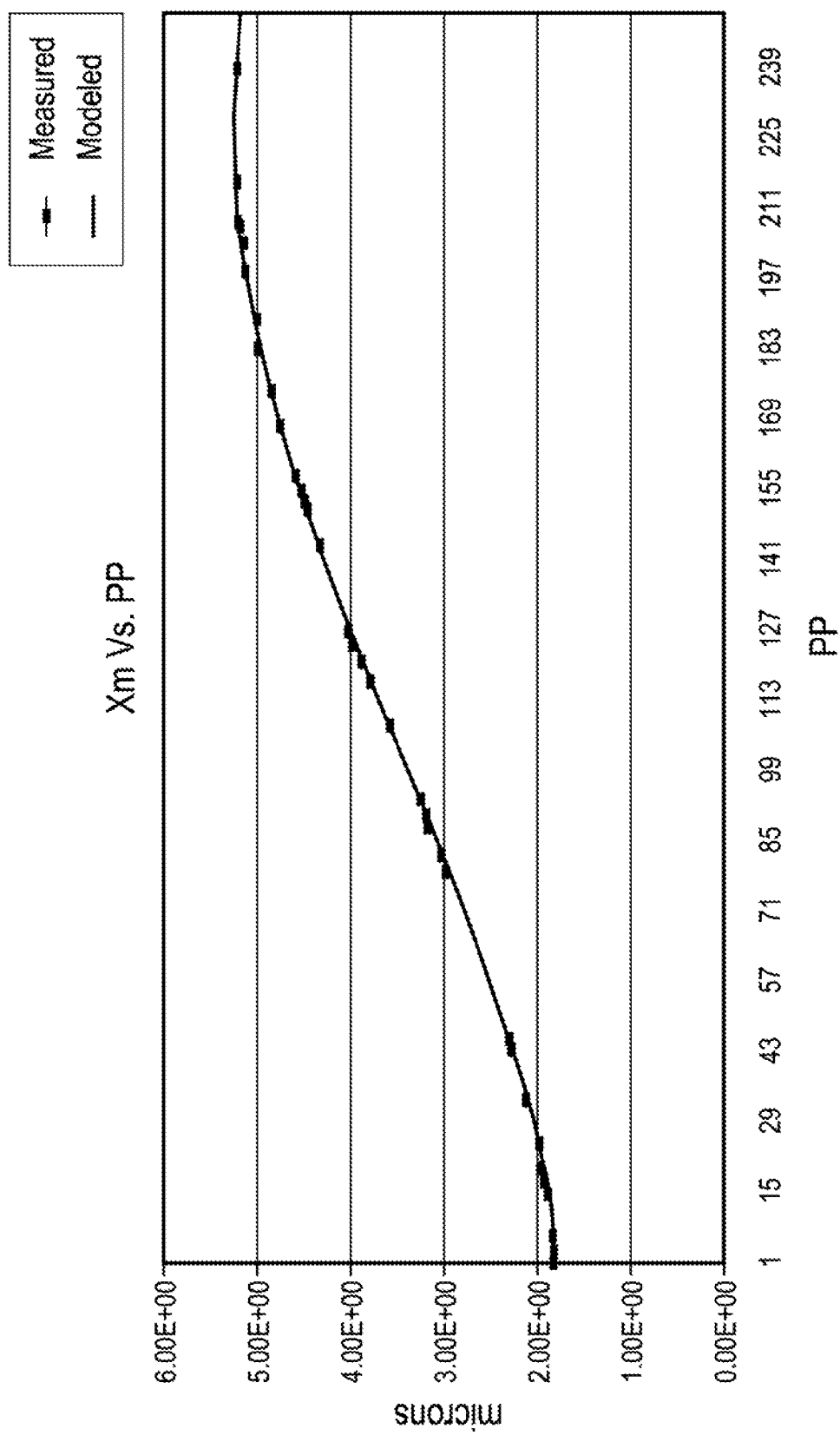
FIG. 18 shows the close correspondence between measured and modeled Xm as contemplated by an embodiment of the present invention.

In eqn. 6 Boldface $\mathbf{X}_m$ is used to represent the ensemble of $X_m$ over all PP. For the case of FIG. 17 a search was done that yielded the following parameters for the model. FIG. 18 shows the close correspondence between measured $X_m$ and modeled $X'_m$.

TABLE 2

Model Parameter Values

| Model Parameter | Parameter Value |
|---|---|
| R | 18.58μ |
| Θ | 18.48° |
| ζ | −0.035 |
| A | 1μ |
| B | −0.004 μ/PP |
| C | −1.49e-5 μ/PP² |

For this solution a total RMS error of 3.35e-3 was achieved. Note that parameters B and C may be left out of the equation (or set to 0) without substantially affecting the results. Thus, useful implementations of the method of the invention may be carried out without consideration of parameters B and C.

Focal Tracking Implementation

Figure 19:
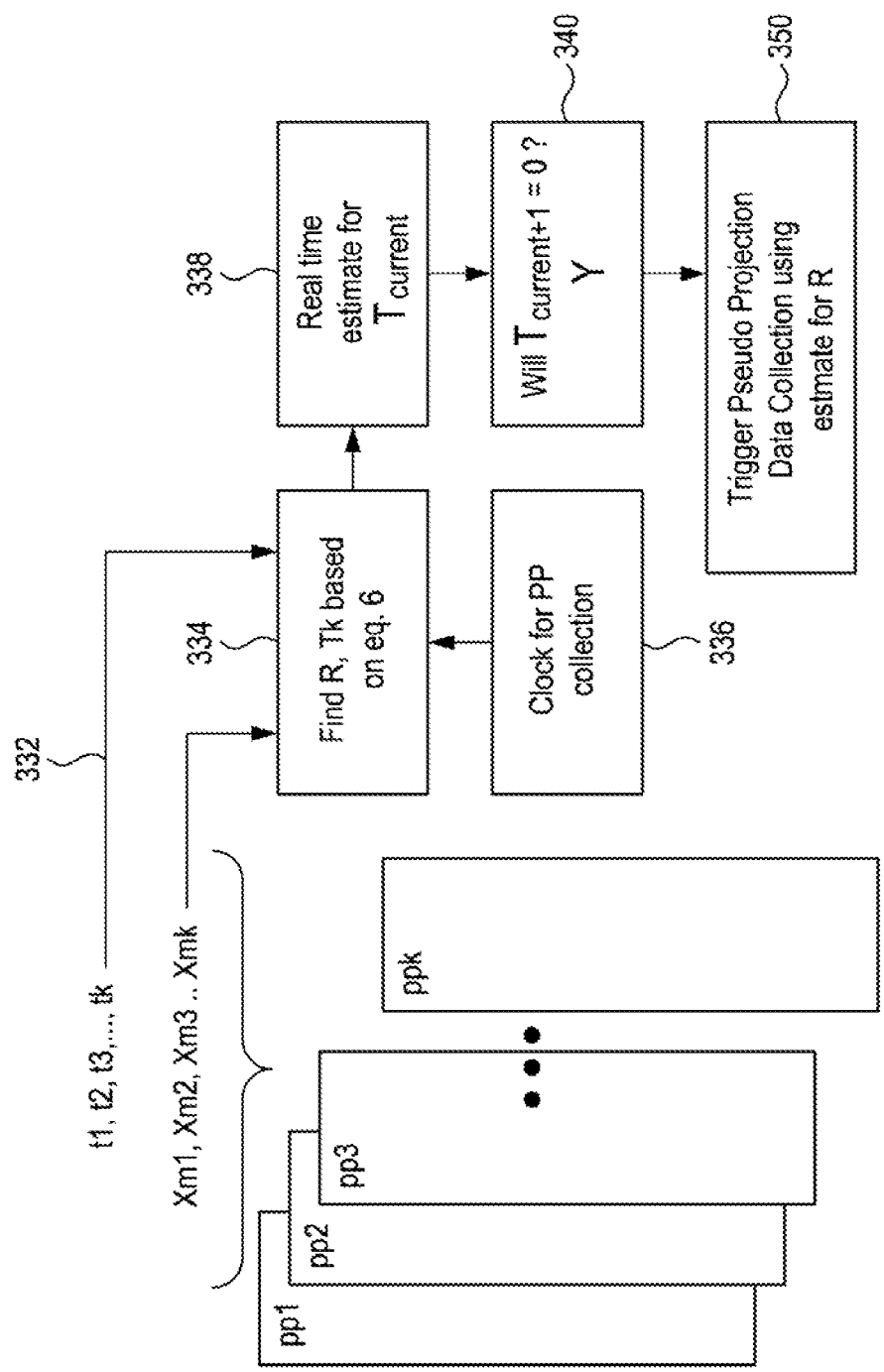
FIG. 19 schematically shows an example flow diagram illustrating the operation of a focal tracking block diagram of the method of the invention.

Referring now to FIG. 19, a focal tracking block diagram of the method of the invention is shown. The analysis of the previous section shows that the parameters for proper focal tracking may be estimated with small error by fitting measured values for $X_m$ with the model of eqn. 5. In the optical tomography system as contemplated by the present invention, when a desired object comes into view it is necessary to find R and to estimate when the object center passes through the zero axis so that image capture for reconstruction may be initiated. A set of k images pp1-ppk are collected at step 330 just after the object is identified for capture, where k may be any number of images useful for reconstructing a 3-D image. The set of k images are collected with an initial estimate for R. It is not necessary to collect the set of k images when the object is placed in any specific way since the set of k images will be used to estimate the true value of R and establish the trigger point for collecting the pseudoprojection images to be used for reconstruction. Center of mass values for X components $X_{m1}$, $X_{m2}$, $X_{m3}$ ... $X_{mk}$ are found for the object in pseudoprojections pp1-ppk and the time of collection t1, t2, t3, ..., $t_k$ for each image is also recorded at step 332. R and the value of Θ at time $t_k$ are computed at step 334. Based on this data and the clock for PP collection 336 the real time value of Θ is estimated at step 338. This value is tested for proximity to the value 0 at step 340. When Θ is anticipated to be 0 on the next clock cycle the trigger for capture of the 250 set of pseudoprojections is enabled at step 350.

Proper functioning of the controller that rotates the micro capillary tube may be checked for by comparing the value ζ against a criterion. ζ in excess of the criterion initiates a service call and causes data to be discarded.

Parameter A gives the average error for micro-capillary tube centration. This value may be compared against a specification for it. A value of A in excess of the specification stops data collection and alerts the user that the tube needs to be re-centered.

Figure 20:
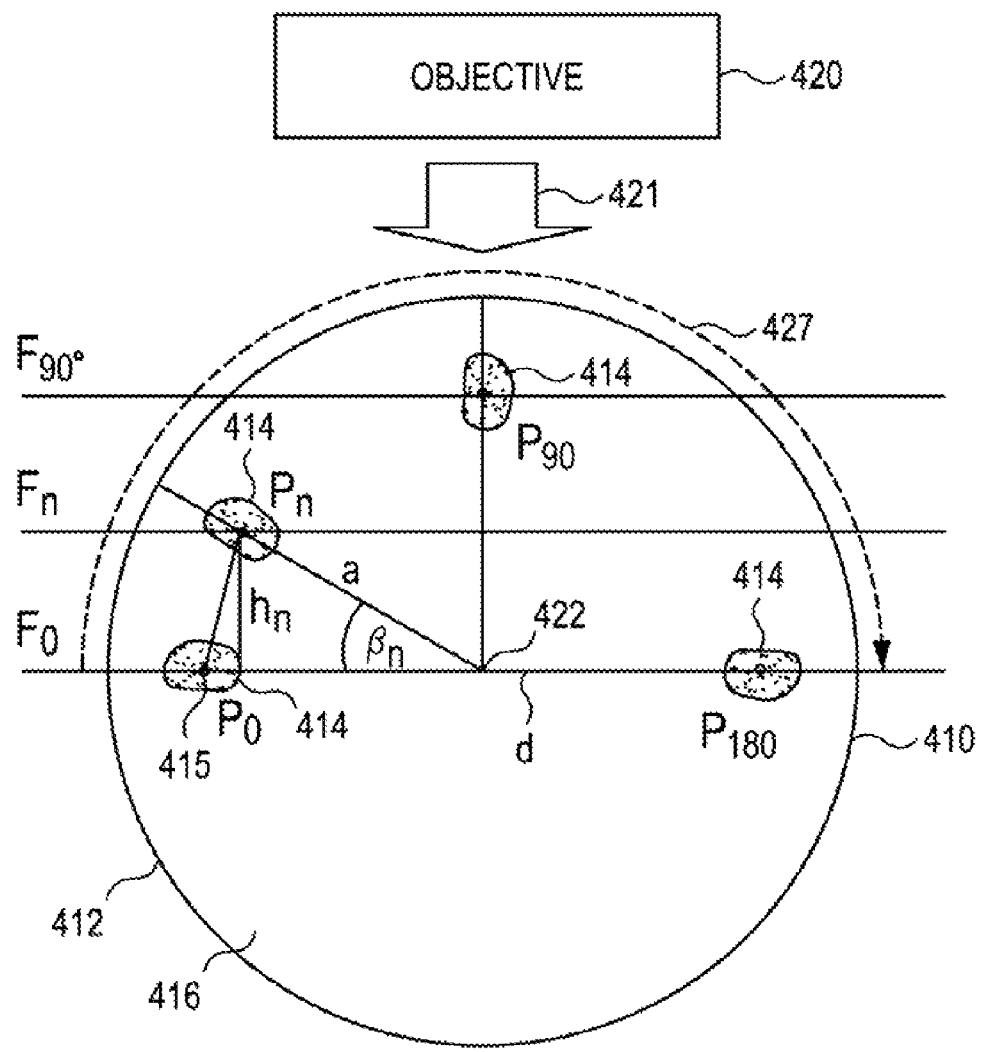
FIG. 20 schematically shows a capillary tube during rotation.

Referring now to FIG. 20 a schematic of capillary tube during rotation is shown for the purpose of illustrating yet another embodiment of the invention. The capillary tube 410 has inner wall 412 with a diameter d and center of rotation 422 which is the center of the capillary tube.

A specimen including an object 414 is held in place with respect to the capillary tube inner wall 412 by a suitable gel 16 or equivalent substance substantially filling the capillary tube 410. An objective lens 420 is positioned to view the object 414. While not so limited, the object 414 may comprise, for example, a biological specimen including a cell, or more particularly a structure of interest within a cell, such as a cell nucleus stained with absorptive dye.

The object 414 is shown at a plurality of positions $P_0$, $P_n$, $P_{90}$, and $P_{180}$, where each of the plurality of positions illustrates a position at different times during rotation of the capillary tube 410. For example, position $P_0$ represents the position where the center of mass of object 414 is coincident with the focal plane that bisects the capillary tube. Focal plane $F_0$ may advantageously be located in a plane perpendicular to an optical axis of the objective lens 420. In contrast, position $P_{90}$ lies in a plane along the optical axis of objective lens 420, or at an angle of 90° relative to focal plane $F_0$. The distance h between $F_0$ and $F_n$ is largest at 90°, where it equals value a. Position $P_n$ corresponds to a position at an angle $β_n$ relative to focal plane $F_0$. Only the inner walls of the capillary tube are shown. The path of the specimen depends on its distance to the center of rotation 422.

In one useful example embodiment of the process of the invention for adjusting the focal-plane tracking, the focus is first set to $F_0$, which is achieved by focusing on the inner tube walls at the section were they are spaced apart the farthest. An optional method for determining $F_0$ is to find the optical contrast reversal zero-crossing at the inner tube wall. Optimal focus may be achieved by an operator looking through the lens, or, more preferably, by machine vision algorithms locating the sharpest edge within the image while focus is adjusted by computer control. The tube is then rotated until the specimen is at a maximum distance to the center 422 and in the same focal plane $F_0$ as the tube walls at the widest separation. A centroid of the structure of interest is located and marked with a cursor or using standard machine visions algorithms. A distance of the centroid to the center of rotation is measured using available machine vision tools. Useful machine vision tools may be constructed from languages such as, for example, Labview™ software from National Instruments of Austin, Tex. The measured distance value is used for calculating a change of focal plane ($h_n$) at a corresponding rotation angle ($β_n$), using the equation $F_n = F_0 + (a \sin(β_n))$. $h_n$ is then converted into a signal which is sent to the piezoelectric objective positioner, that moves the objective in a sinusoidal function according to the translating centroid of the specimen.

For example, if a is measured to be 10 μm, the specimen will move 0.174 μm out of the focal plane during 1° of rotation. At 90°, $F_n$ will be 10 μm apart from $F_0$, and at 180° $F_0$ and $F_n$, will be equal.

Figure 21:
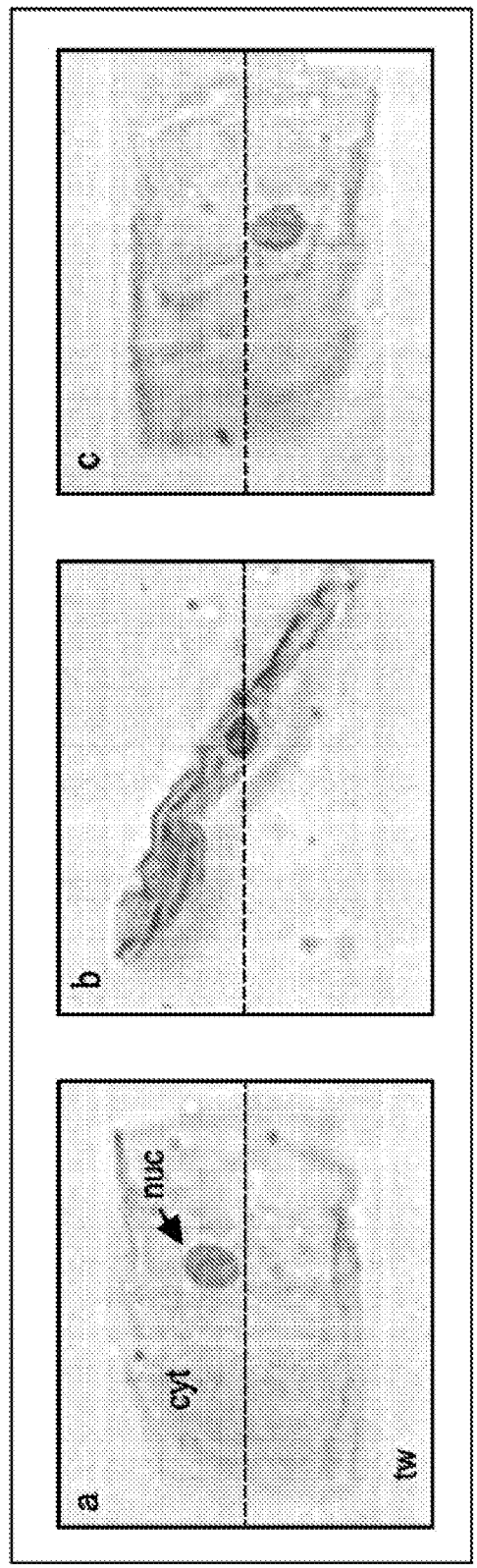
FIG. 21a, FIG. 21b and FIG. 21c show images of a single squamous cell during imaging in an optical tomography microscope.

Referring now to FIG. 21a, FIG. 21b and FIG. 21c where images of a single squamous cell during imaging in the Optical Projection Tomography Microscope are shown. The cell includes a nucleus nuc, surrounded by cytoplasm cyt within capillary tube wall tw. FIG. 21a shows a cell in a starting position where the cell is rotated to a position where its nucleus is in maximum distance to the center of the tube. FIG. 21b shows a cell after 90° rotation. The nucleus appears now in the center of the tube. FIG. 21c shows a cell where the position of the nucleus is at the end of the 180° rotation cycle. The tube walls tw are shown as horizontal lines above and below the cell in FIG. 21a to FIG. 21c. The fragmented line symbolizes the center of the capillary tube (tw=tube wall, cyt=cytoplasm, nuc=nucleus).

A method of testing the focal-plane tracking is to bring the object 414 into the starting position $P_0$. A centroid 415 is marked, and the specimen is then rotated until it is positioned exactly in the middle between the two tube walls, without changing the focus. In one implementation, data acquisition is started before rotation of the capillary tube begins. Upon rotating the tube the object should come into focus at the middle of a cycle. If pseudoprojections are obtained, the object should come into focus at number 125 out of 250 pseudoprojections.

Variables such as direction of object motion and object velocity during rotation can also aid in determining the object radius and angle. Typically an extended depth of field image, as for example, pseudoprojection, obtained by scanning objective lens during single exposure onto camera, is used to create the images because no prior knowledge of object location is required. The maximum depth of field of the image is the inner diameter of the tube.

Since overscanning often leads to loss of resolution and contrast in an extended depth-of-field image, it is advantageous to optimize the depth-of-field extension so that it encompasses the object without significant overscanning. An optimized depth-of-field extension may be determined by measuring the extent of the object. The extent of the object may then be used to minimize the range of scanning to create the extended depth-of-field pseudoprojection image. Using the image data acquired during calibration for object tracking (or additional image data can be acquired if desired), the extent of the object may be determined. By determining the extent of the object along the direction perpendicular to the tube axis for at least two angles, the minimum scan range can be found. The two viewing angles chosen must be 90 degrees apart.

For example, by finding the object extent at the 0 degree position, the minimum scan range is found by rotating the object to the 90 degree position. Likewise, by measuring the object extent when the object is at the 90 degree position, the minimum scan range at 0 and 180 degrees may be determined. Short of taking many images through a minimum rotation of 90 degrees to determine the largest extent of the object, two extended depth-of-field measurements of the object extent may be taken at a first rotation angle $\theta$ and a second rotation angle $\theta+90°$ and a worst case value for object extent may be calculated according to the relationship:

$$\text{object\_extent} = \sqrt{((\text{extent}_\theta)^2 + (\text{extent}_{\theta+90°})^2)}.$$

Reducing the objective lens scanning range may be required to increase image quality either for calibration accuracy, or for contrast-preservation in pseudoprojection used for 3D reconstruction. In this case the range of scanning is subdivided into parts, and multiple extended depth-of-field images acquired.

In another embodiment of the method of the invention the control signals move the objective lens sinusoidally according to a translating centroid of the object. Where the tube has a rotation cycle, the distance value and a set of angle values may be used to compute a proportional sinusoidal function for objective lens position. The sinusoidal function will have a wavelength proportional to the rotational cycle.

In yet another embodiment of the method of the invention the step of creating a projection image of the object being rotated comprises centering the projection image within a circle of reconstruction during tomographic reconstruction. The sinusoidal function may be modulated by an additional function, such as, for example, a derivative of the sinusoidal function, to further control the scanning of the objective lens to form a pseudoprojection. Using a secondary function, such as a derivative, operates to more precisely preserve higher spatial frequencies and image contrast in resultant images of an object, cell, structure or other items of interest during rotation.

Other variations of method of the invention generally recognize that movement of the focal plane may not be equivalent to movement of the objective lens. More particularly, it is the movement of a focal plane through an object that matters for optical projection tomographic imaging. Since imaging errors could be due to first order spherical aberrations, in one example variation, basic sine wave function focal plane adjustments as described above are pre-distorted with pre-compensation values to correct for axial shifts in best focus across the entire field.

In yet another example, a pre-compensation look-up table for adjusting the focal plane is performed using isolated microspheres located at different regions of the field. In yet another example, a pre-compensation calibration using a specific capillary tube sandwich is performed before scanning each sample. In still another example, a pre-compensation for adjusting the focal plane is performed while the tube is rotating rather than using the static tube in the sandwich to account for eccentricities of the tube. In yet another example, the focal plane is pre-compensation for thickness variations of gel as cell is rotated.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. An optical tomography system comprising:
    a light source for illuminating an object of interest with a plurality of radiation beams;
    an object containing tube, wherein when the object of interest is held within the object containing tube it is illuminated by the plurality of radiation beams to produce emerging radiation from the object containing tube;
    an objective lens, having an optical axis, for scanning the object at a set of viewing angles to generate a set of pseudoprojection images from the emerging radiation, where each pseudoprojection image is produced by integrating a series of images from a series of focal planes integrated along the optical axis for each angle;
    a detector array located to receive the set of pseudoprojection images; and
    means for tracking the object of interest responsively to the imaging data, wherein the tracking means comprises means for tracking a pseudoprojection image center.

2. The system of claim 1 wherein the tracking means further comprises means for tracking a focal plane.

3. The optical tomography system of claim 1 wherein the plurality of radiation beams comprise a plurality of parallel radiation beams.

* * * * *